United States Patent
Yauch et al.

(10) Patent No.: US 9,925,240 B2
(45) Date of Patent: Mar. 27, 2018

(54) METHODS OF TREATING AND PREVENTING CANCER DRUG RESISTANCE

(71) Applicant: Genentech, Inc., South San Francisco, CA (US)

(72) Inventors: Robert L. Yauch, Redwood City, CA (US); Xiaofen Ye, Foster City, CA (US); Avi Ashkenazi, San Mateo, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/029,960

(22) PCT Filed: Mar. 6, 2014

(86) PCT No.: PCT/US2014/021120
§ 371 (c)(1),
(2) Date: Apr. 15, 2016

(87) PCT Pub. No.: WO2014/138364
PCT Pub. Date: Sep. 12, 2014

(65) Prior Publication Data
US 2016/0250287 A1    Sep. 1, 2016

Related U.S. Application Data

(60) Provisional application No. 61/773,720, filed on Mar. 6, 2013.

(51) Int. Cl.
| | | |
|---|---|---|
| A61K 31/517 | (2006.01) | |
| A61K 31/519 | (2006.01) | |
| A61K 38/17 | (2006.01) | |
| A61K 45/06 | (2006.01) | |
| A61K 31/5377 | (2006.01) | |

(52) U.S. Cl.
CPC .......... *A61K 38/179* (2013.01); *A61K 31/517* (2013.01); *A61K 31/519* (2013.01); *A61K 31/5377* (2013.01); *A61K 45/06* (2013.01)

(58) Field of Classification Search
CPC ............................. A61K 31/517; A61K 31/519
See application file for complete search history.

(56) References Cited

FOREIGN PATENT DOCUMENTS

WO    2004/096224 A2    11/2004
WO    2008/127719 A1    10/2008

OTHER PUBLICATIONS

ERLOTINIB Registry record (retrieved from STN on Dec. 16, 2016).*
PD173074 Registry record (retrieved from STN on Dec. 16, 2016).*
Suda et al., J. Thorac. Oncol. 16, 1152-61 (2011).*
Thomson et al., Clin. Exp. Metastasis 25, 843-54 (2008).*
Yauch et al., Clin. Cancer Res. 11, 8686-98 (2005).*
Schmid et al., Br. J. Cancer 103, 622-28 (2010).*
Han et al., "Unmet Needs in the Treatment of Metastatic Non-small-cell Lung Cancer", Lung Cancer, Touch Briefings 2008: 27-30 (2008), XP055117048, URL:http://www.touchoncology.com/system/files/private/articles/18407/pdf/han.pdf).
Ho et al., "Fibroblast growth factor receptor 4 regulates proliferation, anti-apoptosis and alpha-fetoprotein secretion during hepatocellular carcinoma progression and represents a potential target for therapeutic intervention", J Hepatol. 50(1):118-27 (2009).
Ilie et al., "Pitfalls in Lung Cancer Molecular Pathology: How to Limit them in Routin Practice?", Curr Med Chem 19:2638-2651 (2012).
International Preliminary Report on Patentability issued in International Application No. PCT/US2014/021120, dated Sep. 8, 2015 (in 9 pages).
International Search Report issued in International Application No. PCT/US2014/021120, dated May 22, 2014 (in 5 pages).
Lin et al., "Combined Treatment of Curcumin and Small Molecule Inhibitors Suppresses Proliferation of A549 and H1299 Human Non-Small-Cell Lung Cancer Cells", Phytotherapy Res., 26:122-126 (2012).
Pardo et al., "The Fibroblast Growth Factor Receptor Inhibitor PD173074 Blocks Small Cell Lung Cancer Growth In vitro and In vivo", Cancer Research, 69(22):8645-8651 ( 2009).
Terai et al., "Activation of the FGF2-FGFR1 Autocrine Pathway: A Novel Mechanism of Acquired Resistance to Gefitinib in NSCLC", Mol Cancer Res. 11(7):759-767 ( 2013).
Berger et al., "Expression of the Multidrug Resistance-Associated Protein (MRP) and Chemoresistance of Human Non-Small-Cell Lung Cancer Cells" Int. J. Cancer 73:84-93 (1997).
Fischer, H. et al., "Fibroblast growth factor receptor-mediated signals contribute to the malignant phenotype of non-small cell lung cancer cells: therapeutic implications and synergism with epidermal growth factor receptor inhibition" Molecular Cancer Therapeutics 7(10):3408-3419 ( 2008).
Ware et al., "Rapidly Acquired Resistance to EGFR Tyrosine Kinase Inhibitors in NSCLC Cell Lines through De-Repression of FGFR2 and FGFR3 Expression" PLos ONE 5(11):1-9 (Nov. 2010).

* cited by examiner

*Primary Examiner* — Theodore R West
(74) *Attorney, Agent, or Firm* — Jessica L. Richardson

(57) ABSTRACT

Provided herein are combination therapies for the treatment of pathological conditions, such as cancer, using an antagonist of FGFR signaling.

12 Claims, 12 Drawing Sheets

| symbol | logFC | t-stat | adj p-value |
|---|---|---|---|
| FGFR1 | 1.1 | 12.0 | 2.57E-09 |
| FGFR2 | -0.8 | -11.5 | 4.57E-09 |
| FGFR3 | -4.0 | -30.9 | 5.54E-16 |
| FGFR4 | -0.3 | -2.6 | 0.044 |
| FGF1 | 0.3 | 2.9 | 0.023 |
| FGF2 | 4.4 | 31.5 | 3.97E-16 |
| FGF3 | -0.4 | -4.5 | 0.001 |
| FGF4 | -0.2 | -1.8 | 0.174 |
| FGF5 | 0.5 | 3.7 | 0.005 |
| FGF6 | -0.2 | -2.2 | 0.088 |
| FGF7 | 0.0 | -0.1 | 0.965 |
| FGF8 | -0.1 | -0.5 | 0.722 |
| FGF9 | 0.3 | 3.1 | 0.016 |
| FGF10 | 0.1 | 0.7 | 0.651 |
| FGF11 | -0.8 | -13.0 | 6.64E-10 |
| FGF13 | -0.4 | -4.7 | 0.0006 |
| FGF14 | 0.0 | 0.2 | 0.920 |
| FGF16 | 0.0 | 0.3 | 0.831 |
| FGF17 | 0.0 | 0.1 | 0.957 |
| FGF18 | -0.1 | -1.2 | 0.379 |
| FGF19 | -5.2 | -25.6 | 1.11E-14 |
| FGF20 | 0.0 | -0.3 | 0.863 |
| FGF21 | -0.3 | -3.2 | 0.015 |
| FGF22 | -0.2 | -2.2 | 0.095 |
| FGF23 | 0.0 | 0.0 | 0.985 |
| CDH2 | 1.0 | 12.2 | 1.78E-09 |

| Drug | Primary Target/MOA | IC₅₀ (µM) HCC4006 - erlotinib | HCC4006-ER - erlotinib | HCC4006-ER + erlotinib (1µM) |
| --- | --- | --- | --- | --- |
| erlotinib | EGFR Inhibitor | 0.12 | >5 | NA |
| Paciltaxel | Microtubule stabilizer, anti-mitotic | <0.001 | <0.001 | <0.001 |
| Gemcitabine | Anti-metabolite | 0.16 | 0.56 | >5 |
| Dasatinib | BCR-ABL/Src Inhibitor | 0.16 | 0.14 | 0.065 |
| Trichostatin A | HDAC Inhibitor (pan-HDAC) | 0.24 | 0.18 | 0.13 |
| GDC-0980 | P13K and mTOR Inhibitor | 0.70 | 1.34 | 0.88 |
| salinomycin | antibacterial/coccidiostat Ionophore | 1.9 | 2.6 | 3.3 |
| GDC-0941 | P13K Inhibitor | 2.1 | 4.4 | 2.3 |
| BMS-536924 | IGF1R Inhibitor | 2.2 | 4.3 | >5 |
| Entinostat (MS-275) | HDAC Inhibitor (class 1 selective) | 2.6 | 4.4 | 3.4 |
| PD-0325901 | MEK Inhibitor | 4.4 | 3.9 | 3.0 |
| PF-2341066 | MET/ALK | >5 | >5 | 3.6 |
| GDC-0917 | Monomer IAP Antagonist | >5 | >5 | >5 |
| ABT263 | BCL-XL/BCL2 (Navitoclax) | >5 | >5 | >5 |
| Cisplatin | Alkylating agent | >5 | >5 | >5 |
| CPT-11 | Type 1 topoisomerase Inhibitor | >5 | >5 | >5 |
| G-425652 | P1M1/2/3 Inhibitor | >5 | >5 | >5 |
| SB43152 | TGFRBR1 Inhibitor | >5 | >5 | >5 |
| GDC-0425 | Chk1 Inhibitor | >5 | >5 | >5 |
| BIRB-796 | p38alpha Inhibitor | >5 | >5 | >5 |
| A769662 | AMPK activator | >5 | >5 | >5 |
| NFkBI | NFkB Inhibitor | >5 | >5 | >5 |
| Go5976 | PRKCA/PRKCB Inhibitor | >5 | >5 | >5 |
| PD173074 | FGFR1/3 Inhibitor | >5 | >5 | 0.46 |
| Imatinib | ABL1/KIT/PDGFRA | >5 | >5 | >5 |
| Sunitinib | PDGFRA/KIT/FLT3 | >5 | >5 | >5 |
| SP600125 | JNK Inhibitor | >5 | >5 | >5 |
| BI-D1870 | Rsk Inhibitor | >5 | >5 | >5 |
| CHIR 98014 | GSK3 Inhibitor | >5 | >5 | >5 |

FIG. 8

METHODS OF TREATING AND PREVENTING CANCER DRUG RESISTANCE

RELATED APPLICATIONS

This application is a 371 application of International Application No. PCT/US2014/021120, filed on Mar. 6, 2014, which claims priority to U.S. patent application No. 61/773,720 filed Mar. 6, 2013, the entire contents of which are incorporated herein by their entireties.

FIELD

Provided herein are combination therapies for the treatment of pathological conditions, such as cancer, using antagonists of FGFR signaling.

BACKGROUND

The relatively rapid acquisition of resistance to cancer drugs remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways, epigenetic alterations). Treatment of NSCLC patients harboring activating EGFR mutations with EGFR tyrosine kinase inhibitors results in anti-tumor responses to therapy, however patients ultimately progress on therapy due to the acquisition of drug resistance. Known mechanisms of resistance include secondary mutations in the EGFR gene (EGFR$^{T790M}$) or MET gene amplification, however the underlying mechanism of resistance remains to be elucidated in ~40-45% of cases. New treatment methods are needed to successfully address heterogeneity within cancer cell populations and the emergence of cancer cells resistant to drug treatments.

SUMMARY

Provided herein are combination therapies using antagonists of FGFR signaling and EGFR antagonists.

In particular, provided herein are methods of treating cancer in an individual comprising concomitantly administering to the individual (a) an antagonist of FGFR signaling and (b) an EGFR antagonist. In some embodiments, the respective amounts of the antagonist of FGFR signaling and the EGFR antagonist are effective to increase the period of cancer sensitivity and/or delay the development of cancer resistance to the EGFR antagonist. In some embodiments, the respective amounts of the antagonist of FGFR signaling and the EGFR antagonist are effective to increase efficacy of a cancer treatment comprising EGFR antagonist. For example, in some embodiments, the respective amounts of the antagonist of FGFR signaling and the EGFR antagonist are effective to increased efficacy compared to a standard treatment comprising administering an effective amount of EGFR antagonist without (in the absence of) the antagonist of FGFR signaling. In some embodiments, the respective amounts of the antagonist of FGFR signaling and the EGFR antagonist are effective to increased response (e.g., complete response) compared to a standard treatment comprising administering an effective amount of the EGFR antagonist without (in the absence of) the antagonist of FGFR signaling. In some embodiments, the respective amounts of the antagonist of FGFR signaling and the EGFR antagonist are effective to increase cancer sensitivity and/or restore sensitivity to the EGFR antagonist.

Provided herein are also methods of treating a cancer cell, wherein the cancer cell is resistant to treatment with an EGFR antagonist in an individual comprising administering to the individual an effective amount of an antagonist of FGFR signaling and an effective amount of the EGFR antagonist. In addition, provided herein are methods of treating cancer resistant to an EGFR antagonist in an individual comprising administering to the individual an effective amount of an antagonist of FGFR signaling and an effective amount of the EGFR antagonist.

Provided herein are methods of increasing sensitivity and/or restoring sensitivity to an EGFR antagonist comprising administering to the individual an effective amount of an antagonist of FGFR signaling and an effective amount of the EGFR antagonist.

Also provided herein are methods of increasing efficacy of a cancer treatment comprising an EGFR antagonist in an individual comprises concomitantly administering to the individual (a) an effective amount of an antagonist of FGFR signaling and (b) an effective amount of the EGFR antagonist.

Provided herein are methods of treating cancer in an individual wherein cancer treatment comprising concomitantly administering to the individual (a) an effective amount of an antagonist of FGFR signaling and (b) an effective amount of an EGFR antagonist, wherein the cancer treatment has increased efficacy compared to a standard treatment comprising administering an effective amount of the EGFR antagonist without (in the absence of) antagonist of FGFR signaling.

In addition, provided herein are methods of delaying and/or preventing development of cancer resistant to an EGFR antagonist in an individual, comprising concomitantly administering to the individual (a) an effective amount of an antagonist of FGFR signaling and (b) an effective amount of the EGFR.

Provided herein are methods of treating an individual with cancer who has increased likelihood of developing resistance to an EGFR antagonist comprising concomitantly administering to the individual (a) an effective amount of an antagonist of FGFR signaling and (b) an effective amount of the EGFR antagonist.

Further provided herein are methods of increasing sensitivity to an EGFR antagonist in an individual with cancer comprising concomitantly administering to the individual (a) an effective amount of an antagonist of FGFR signaling and (b) an effective amount of the EGFR antagonist.

Provided herein are also methods extending the period of an EGFR antagonist sensitivity in an individual with cancer comprising concomitantly administering to the individual (a) an effective amount of an antagonist of FGFR signaling and (b) an effective amount of the EGFR antagonist.

Provided herein are methods of extending the duration of response to an EGFR antagonist in an individual with cancer comprising concomitantly administering to the individual (a) an effective amount of an antagonist of FGFR signaling and (b) an effective amount of the EGFR antagonist.

In some embodiments of any of the methods, the antagonist of FGFR signaling is an antibody inhibitor, a small molecule inhibitor, a binding polypeptide inhibitor, and/or a polynucleotide antagonist. In some embodiments, the antagonist of FGFR signaling is a binding polypeptide inhibitor. In some embodiments, the binding polypeptide inhibitor comprises a region of the extracellular domain of FGFR linked to a Fc domain (e.g., a region of the extracellular domain of FGFR linked to an immoglobulin hinge and Fc domains). In some embodiments, the antagonist of FGFR signaling is an antagonist of FGFR1 signaling. In some embodiments, the antagonist of FGFR signaling is an antagonist of FGFR2 signaling. In some embodiments, the antagonist of FGFR signaling is an antagonist of FGFR3 signaling. In some embodiments, the antagonist of FGFR signaling is an antagonist of FGFR4 signaling. In some embodiments, the antagonist of FGFR signaling is a small molecule. In some embodiments, the antagonist of FGFR signaling is an antibody.

In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the small molecule is N-[2-[[4-(diethylamino)butyl]amino]-6-(3,5-dimethoxyphenyl)pyrido[2,3-d]pyrimidin-7-yl]-N'-(1,1-dimethylethyl)-urea or pharmaceutically acceptable salt thereof. In some embodiments, the small molecule is BGJ398 (Novartis), AZD4547 (AstraZeneca), and/or FF284 (Chugai/Debiopharm (Debio 1347). In some embodiments, the antagonist of FGFR1 signaling is an anti-FGF2 antibody. In some embodiments, the antagonist of FGFR1 signaling is an anti-FGFR1 antibody. In some embodiments, the antagonist of FGFR1 signaling is an anti-FGFR1-IIIb antibody. In some embodiments, the antagonist of FGFR1 signaling is an anti-FGFR1-IIIc antibody. In some embodiments the antagonist of FGFR signaling is an anti-FGFR antibody capable of binding more than one FGFR polypeptide.

In some embodiments of any of the methods, the EGFR antagonist is N-(3-ethynylphenyl)-6,7-bis(2-methoxyethoxy)-4-quinazolinamine and/or a pharmaceutical acceptable salt thereof. In some embodiments, the EGFR antagonist is N-(3-ethynylphenyl)-6,7-bis(2-methoxyethoxy)-4-quinazolinamine. In some embodiments of any of the methods, the EGFR antagonist is N-(3-chloro-4-fluoro-phenyl)-7-methoxy-6-(3-morpholin-4-ylpropoxy)quinazolin-4-amine and/or a pharmaceutical acceptable salt thereof. In some embodiments, the EGFR antagonist is N-(3-chloro-4-fluoro-phenyl)-7-methoxy-6-(3-morpholin-4-ylpropoxy) quinazolin-4-amine.

In some embodiments of any of the methods, the cancer is lung cancer. In some embodiments, the lung cancer is NSCLC. In some embodiments, the cancer has undergone epithelial-mesenchymal transition.

BRIEF DESCRIPTION OF THE FIGURES

FIG. 8 | A screen of a panel of small molecule inhibitors in HCC4006-ER cells in the presence or absence of erlotinib revealed that the FGFR inhibitor, PD173074, could reverse resistance to erlotinib. Growth inhibitor $IC_{50}$s are shown.

DETAILED DESCRIPTION

I. Definitions

Figure 1A:
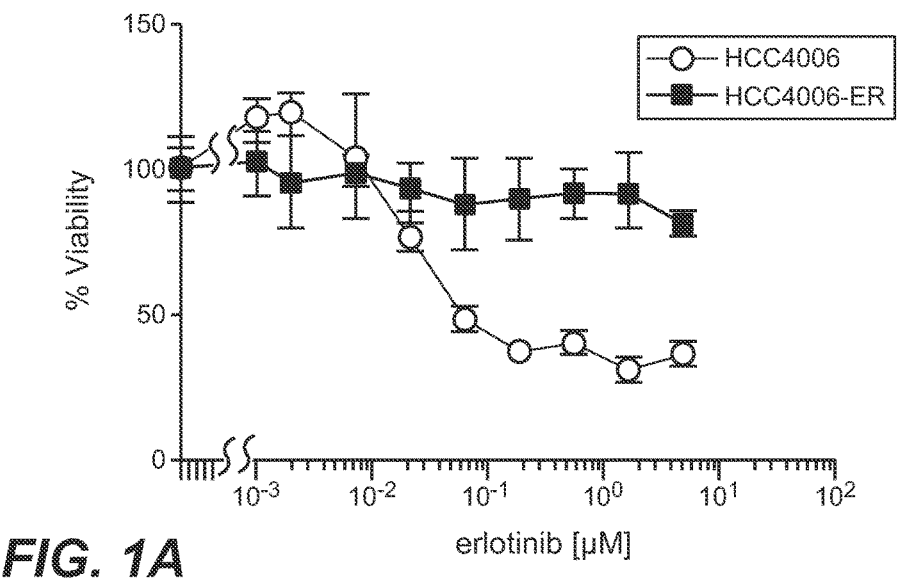
FIG. 1A-C. | HCC4006-ER cells are resistant to erlotinib. A, Cell viability in parental (HCC4006) and erlotinib-selected HCC4006 cells (HCC4006-ER) was assayed at 72 h in the presence of the indicated concentrations of erlotinib. B, HCC4006 and HCC4006-ER cells were treated with or without 1 µM erlotinib for 72 h, stained with propidium iodide (PI) and annexin V and analysed by FACS to quantitate annexin-positive cells. C, HCC4006 and HCC4006-ER cells were treated with the indicated concentrations of erlotinib for 8 h and cell lysates were immunoblotted with the indicated antibodies.

An "antagonist" (interchangeably termed "inhibitor") of a polypeptide of interest is an agent that interferes with activation or function of the polypeptide of interest, e.g., partially or fully blocks, inhibits, or neutralizes a biological activity mediated by a polypeptide of interest. For example, an antagonist of polypeptide X may refers to any molecule that partially or fully blocks, inhibits, or neutralizes a biological activity mediated by polypeptide X. Examples of inhibitors include antibodies; ligand antibodies; small molecule antagonists; antisense and inhibitory RNA (e.g., shRNA) molecules. Preferably, the inhibitor is an antibody or small molecule which binds to the polypeptide of interest. In a particular embodiment, an inhibitor has a binding affinity (dissociation constant) to the polypeptide of interest of about 1,000 nM or less. In another embodiment, inhibitor has a binding affinity to the polypeptide of interest of about 100 nM or less. In another embodiment, an inhibitor has a binding affinity to the polypeptide of interest of about 50 nM or less. In a particular embodiment, an inhibitor is covalently bound to the polypeptide of interest. In a particular embodiment, an inhibitor inhibits signaling of the polypeptide of interest with an $IC_{50}$ of 1,000 nM or less. In another embodiment, an inhibitor inhibits signaling of the polypeptide of interest with an $IC_{50}$ of 500 nM or less. In another embodiment, an inhibitor inhibits signaling of the polypeptide of interest with an $IC_{50}$ of 50 nM or less. In certain embodiments, the antagonist reduces or inhibits, by at least 10%, 20%, 30%, 40%, 50%, 60%, 70%, 80%, 90% or more, the expression level or biological activity of the polypeptide of interest. In some embodiments, the polypeptide of interest is FGFR receptor (e.g., FGFR1, FGFR2, FGFR3, and/or FGFR4) or FGF (e.g., FGF1-23). In some embodiments, the polypeptide of interest is EGFR.

The term "polypeptide" as used herein, refers to any native polypeptide of interest from any vertebrate source, including mammals such as primates (e.g., humans) and rodents (e.g., mice and rats), unless otherwise indicated. The term encompasses "full-length," unprocessed polypeptide as well as any form of the polypeptide that results from processing in the cell. The term also encompasses naturally occurring variants of the polypeptide, e.g., splice variants or allelic variants.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "small molecule" refers to any molecule with a molecular weight of about 2000 daltons or less, preferably of about 500 daltons or less.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms anti-polypeptide of interest antibody and "an antibody that binds to" a polypeptide of interest refer to an antibody that is capable of binding a polypeptide of interest with sufficient affinity such that the antibody is useful as a diagnostic and/or therapeutic agent in targeting a polypeptide of interest. In one embodiment, the extent of binding of an anti-polypeptide of interest antibody to an unrelated, non-polypeptide of interest protein is less than about 10% of the binding of the antibody to a polypeptide of interest as measured, e.g., by a radioimmunoassay (RIA). In certain embodiments, an antibody that binds to a polypeptide of interest has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-polypeptide of interest antibody binds to an epitope of a polypeptide of interest that is conserved among polypeptides of interest from different species. In some embodiments, the polypeptide of interest is FGFR (e.g., FGFR1, FGFR2, FGFR3, and/or FGFR4) and/or FGF (e.g., FGF1-23). In some embodiments, the polypeptide of interest is EGFR.

A "blocking antibody" or an "antagonist antibody" is one which inhibits or reduces biological activity of the antigen it binds. Preferred blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "immunoconjugate" is an antibody conjugated to one or more heterologous molecule(s), including but not limited to a cytotoxic agent.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metasisis; (5) relief, to some extent, of one or more symptoms associated with the disease or disorder (e.g., cancer); (6) increase in the length of progression free survival; and/or (9) decreased mortality at a given point of time following treatment.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression). The difference between said two values is, for example, less than about 50%, less than about 40%, less than about 30%, less than about 20%, and/or less than about 10% as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

An "effective amount" of a substance/molecule, e.g., pharmaceutical composition, refers to an amount effective, at dosages and for periods of time necessary, to achieve the desired therapeutic or prophylactic result.

A "therapeutically effective amount" of a substance/molecule may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The phrase "pharmaceutically acceptable salt" as used herein, refers to pharmaceutically acceptable organic or inorganic salts of a compound.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "cytotoxic agent" as used herein refers to a substance that inhibits or prevents a cellular function and/or causes cell death or destruction. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu), chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents), growth inhibitory agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "concomitantly" is used herein to refer to administration of two or more therapeutic agents, give in close enough temporal proximity where their individual therapeutic effects overlap in time. Accordingly, concurrent administration includes a dosing regimen when the administration of one or more agent(s) continues after discontinuing the administration of one or more other agent(s). In some embodiments, the concomitantly administration is concurrently, sequentially, and/or simultaneously.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

As is understood by one skilled in the art, reference to "about" a value or parameter herein includes (and describes) embodiments that are directed to that value or parameter per se. For example, description referring to "about X" includes description of "X".

It is understood that aspect and embodiments of the invention described herein include "consisting" and/or "consisting essentially of" aspects and embodiments. As used herein, the singular form "a", "an", and "the" includes plural references unless indicated otherwise.

II. Methods and Uses

Provided herein are methods utilizing an antagonist of FGFR signaling and an EGFR antagonist.

In particular, provided herein are methods of treating cancer in an individual comprising concomitantly administering to the individual (a) an antagonist of FGFR signaling and (b) an EGFR antagonist. In some embodiments, the respective amounts of the antagonist of FGFR signaling and the EGFR antagonist are effective to increase the period of cancer sensitivity and/or delay the development of cancer resistance to the EGFR antagonist. In some embodiments, the respective amounts of the antagonist of FGFR signaling and the EGFR antagonist are effective to increase efficacy of a cancer treatment comprising EGFR antagonist. For example, in some embodiments, the respective amounts of the antagonist of FGFR signaling and the EGFR antagonist are effective to increased efficacy compared to a standard treatment comprising administering an effective amount of EGFR antagonist without (in the absence of) the antagonist of FGFR signaling. In some embodiments, the respective amounts of the antagonist of FGFR signaling and the EGFR antagonist are effective to increased response (e.g., complete response) compared to a standard treatment comprising administering an effective amount of the EGFR antagonist without (in the absence of) the antagonist of FGFR signaling. In some embodiments, the respective amounts of the antagonist of FGFR signaling and the EGFR antagonist are effective to increase cancer sensitivity and/or restoring sensitivity to the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Provided herein are methods of treating a cancer cell, wherein the cancer cell is resistant to treatment with an EGFR antagonist in an individual comprising administering to the individual an effective amount of an antagonist of FGFR signaling and an effective amount of the EGFR antagonist. Also provided herein are methods of treating cancer resistant to an EGFR antagonist in an individual comprising administering to the individual an effective amount of an antagonist of FGFR signaling and an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Provided herein are also methods of increasing sensitivity and/or restoring sensitivity to an EGFR antagonist comprising administering to the individual an effective amount of an antagonist of FGFR signaling and an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Further provided herein are methods of increasing efficacy of a cancer treatment comprising an EGFR antagonist in an individual comprises concomitantly administering to the individual (a) an effective amount of an antagonist of FGFR signaling and (b) an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Provided herein of treating cancer in an individual wherein cancer treatment comprising concomitantly administering to the individual (a) an effective amount of an antagonist of FGFR signaling and (b) an effective amount of an EGFR antagonist, wherein the cancer treatment has increased efficacy compared to a standard treatment comprising administering an effective amount of the EGFR antagonist without (in the absence of) the antagonist of FGFR signaling. In addition, provided herein are methods of delaying and/or preventing development of cancer resistant to an EGFR antagonist in an individual, comprising concomitantly administering to the individual (a) an effective amount of an antagonist of FGFR signaling and (b) an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Provided herein are methods of treating an individual with cancer who has increased likelihood of developing resistance to an EGFR antagonist comprising concomitantly administering to the individual (a) an effective amount of an antagonist of FGFR signaling and (b) an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Further provided herein are methods of increasing sensitivity to an EGFR antagonist in an individual with cancer comprising concomitantly administering to the individual (a) an effective amount of an antagonist of FGFR signaling and (b) an effective amount of the EGFR antagonist. In addition, provided herein are methods of extending the period of an EGFR antagonist sensitivity in an individual with cancer comprising concomitantly administering to the individual (a) an effective amount of an antagonist of FGFR signaling and (b) an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

Provided herein are also methods of extending the duration of response to an EGFR antagonist in an individual with cancer comprising concomitantly administering to the (a) an effective amount of an antagonist of FGFR signaling and (b) an effective amount of the EGFR antagonist. In some embodiments, the antagonist of FGFR signaling is an antagonist of FGFR1 signaling. In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the EGFR antagonist is erlotinib or gefitinib.

In some embodiments of any of the methods, the antagonist of FGFR signaling is an antibody inhibitor, a small molecule inhibitor, a binding polypeptide inhibitor, and/or a polynucleotide antagonist. In some embodiments, the antagonist of FGFR signaling is a binding polypeptide inhibitor. In some embodiments, the binding polypeptide inhibitor comprises a region of the extracellular domain of FGFR linked to a Fc (e.g., FP-1039 (Five Prime)). In some embodiments, the antagonist of FGFR signaling is an antagonist of FGFR1 signaling. In some embodiments, the antagonist of FGFR signaling is an antagonist of FGFR2 signaling. In some embodiments, the antagonist of FGFR signaling is an antagonist of FGFR3 signaling. In some embodiments, the antagonist of FGFR signaling is an antagonist of FGFR4 signaling. In some embodiments, the antagonist of FGFR signaling is a small molecule. In some embodiments, the antagonist of FGFR signaling is an antibody.

In some embodiments, the antagonist of FGFR1 signaling binds to and/or inhibits one or more of FGFR1b, FGFR1c, FGF1, FGF2, FGF3, FGF4, FGF5, FGF6, and FGF10. In some embodiments, the small molecule is N-[2-[[4-(diethylamino)butyl]amino]-6-(3,5-dimethoxyphenyl)pyrido[2,3-d]pyrimidin-7-yl]-N'-(1,1-dimethylethyl)-urea or pharmaceutically acceptable salt thereof. In some embodiments, the small molecule is BGJ398 (Novartis), AZD4547 (AstraZeneca), and/or FF284 (Chugai/Debiopharm (Debio 1347). In some embodiments, the antagonist of FGFR1 signaling is an anti-FGF2 antibody. In some embodiments, the antagonist of FGFR1 signaling is an anti-FGFR1 antibody. In some embodiments, the antagonist of FGFR1 signaling is an anti-FGFR1-IIIb antibody. In some embodiments, the antagonist of FGFR1 signaling is an anti-FGFR1-IIIc antibody. In some embodiments the antagonist of FGFR signaling is an anti-FGFR antibody capable of binding more than one FGFR polypeptide.

Cancer having resistance to a therapy as used herein includes a cancer which is not responsive and/or reduced ability of producing a significant response (e.g., partial response and/or complete response) to the therapy. Resistance may be acquired resistance which arises in the course of a treatment method. In some embodiments, the acquired drug resistance is transcient and/or reversible drug tolerance. Transient and/or reversible drug resistance to a therapy includes wherein the drug resistance is capable of regaining sensitivity to the therapy after a break in the treatment method. In some embodiments, the acquired resistance is permanent resistance. Permanent resistance to a therapy includes a genetic change conferring drug resistance.

Cancer having sensitivity to a therapy as used herein includes cancer which is responsive and/or capable of producing a significant response (e.g., partial response and/or complete response).

Methods of determining of assessing acquisition of resistance and/or maintenance of sensitivity to a therapy are known in the art and described in the Examples. Changes in acquisition of resistance and/or maintenance of sensitivity such as drug tolerance may be assessed by assaying the growth of drug tolerant persisters as described in the Examples and Sharma et al. Changes in acquisition of resistance and/or maintenance of sensitivity such as permanent resistance and/or expanded resisters may be assessed by assaying the growth of drug tolerant expanded persisters as described in the Examples and Sharma et al. In some embodiments, resistance may be indicated by a change in $IC_{50}$, $EC_{50}$ or decrease in tumor growth in drug tolerant persisters and/or drug tolerant expanded persisters. In some embodiments, the change is greater than about any of 50%, 100%, and/or 200%. In addition, changes in acquisition of resistance and/or maintenance of sensitivity may be assessed in vivo for examples by assessing response, duration of response, and/or time to progression to a therapy, e.g., partial response and complete response. Changes in acquisition of resistance and/or maintenance of sensitivity may be based on changes in response, duration of response, and/or time to progression to a therapy in a population of individuals, e.g., number of partial responses and complete responses.

In some embodiments of any of the methods, the cancer is a solid tumor cancer. In some embodiments, the cancer is lung cancer (e.g., non-small cell lung cancer (NSCLC)). In some embodiments, the cancer is cancer of epithelial tissue. In some embodiments, the cancer is adenocarcinoma. The cancer in any of the combination therapies methods described herein when starting the method of treatment comprising the antagonist of FGFR signaling and the EGFR antagonist may be sensitive (examples of sensitive include, but are not limited to, responsive and/or capable of producing a significant response (e.g., partial response and/or complete response)) to a method of treatment comprising the EGFR alone. The cancer in any of the combination therapies methods described herein when starting the method of treatment comprising the antagonist of FGFR signaling and the EGFR antagonist may not be resistant (examples of resistance include, but are not limited to, not responsive and/or reduced ability and/or incapable of producing a significant response (e.g., partial response and/or complete response)) to a method of treatment comprising the EGFR antagonist alone. In some embodiments, the cancer has undergone epithelial-mesenchymal transition (EMT). In some embodiments, EMT is detected by assaying expression of epithelial-associated proteins/RNAs (e.g., E-cadherin) and/or mesenchymal-associate proteins/RNAs (e.g., vimentin). In some embodiments, the cancer has wild-type EGFR (i.e., the cancer does not have a mutation in EGFR). In some embodiments, the cancer has a mutation in EGFR.

In some embodiments of any of the methods, the individual according to any of the above embodiments may be a human.

In some embodiments of any of the methods, the combination therapies noted above encompass combined administration (where two or more therapeutic agents are included in the same or separate formulations), and separate administration, in which case, administration of the antagonist of the invention can occur prior to, simultaneously, sequentially, concurrently, and/or following, administration of the additional therapeutic agent and/or adjuvant. In some embodiments, the combination therapy further comprises radiation therapy and/or additional therapeutic agents.

An antagonist of FGFR signaling and an EGFR antagonist can be administered by any suitable means, including oral, parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antagonists of FGFR signaling (e.g., an antibody, binding polypeptide, and/or small molecule) and an EGFR antagonist described herein may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antagonist of FGFR signaling and an EGFR antagonist need not be, but is optionally formulated with one or more agents currently used to prevent or treat the disorder in question. The effective amount of such other agents depends on the amount of the antagonist of FGFR signaling and an EGFR antagonist present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antagonist of FGFR signaling and an EGFR antagonist described herein (when used alone or in combination with one or more other additional therapeutic agents) will depend on the type of disease to be treated, the severity and course of the disease, whether the antagonist of FGFR signaling and an EGFR antagonist is administered for preventive or therapeutic purposes, previous therapy, the patient's clinical history and response to the antagonist of FGFR signaling and an EGFR antagonist, and the discretion of the attending physician. The antagonist of FGFR signaling and an EGFR antagonist is suitably administered to the patient at one time or over a series of treatments. For repeated administrations over several days or longer, depending on the condition, the treatment would generally be sustained until a desired suppression of disease symptoms occurs. Such doses may be administered intermittently, e.g., every week or every three weeks (e.g., such that the patient receives from about two to about twenty, or e.g., about six doses of the antagonist of FGFR signaling and an EGFR antagonist. An initial higher loading dose, followed by one or more lower doses may be administered. An exemplary dosing regimen comprises administering. However, other dosage regimens may be useful. The progress of this therapy is easily monitored by conventional techniques and assays.

It is understood that any of the above formulations or therapeutic methods may be carried out using an immunoconjugate as the antagonist of FGFR signaling and/or EGFR antagonist.

III. Therapeutic Compositions

Provided herein are combinations comprising an antagonist of FGFR signaling and an EGFR antagonist. In certain embodiments, the combination increases the efficacy of the targeted therapeutic administered alone. In certain embodiments, the combination delays and/or prevents development of cancer resistance to the targeted therapeutic. In certain embodiments, the combination extends the period of the targeted therapeutic sensitivity in an individual with cancer.

Provided herein are antagonists of FGFR signaling and an EGFR antagonist useful in the combination therapy methods described herein. In some embodiments, the antagonists of FGFR signaling and/or EGFR antagonists are an antibody, binding polypeptide, binding small molecule, and/or polynucleotide.

Amino acid sequences of various FGFRs and FGFs are known in the art and are publicly available. See e.g., FGFR1 (e.g., UniProtKB/Swiss-Prot P11362-1, P11362-2, P11362-3, P11362-4, P11362-5, P11362-6, P11362-7, P11362-8, P11362-9, P11362-10, P11362-11, P11362-12, P11362-13, P11362-14, P11362-15, P11362-16, P11362-17, P11362-18, P11362-19, P11362-20, and/or P11362-21), FGFR2 (e.g., UniProtKB/Swiss-Prot P21802-1 (i.e., FGFR2-IIIc), P21802-2, P21802-3 (i.e., FGFR2-IIIb), P21802-4, P21802-5, P21802-6, P21802-7, P21802-8, P21802-9, P21802-10, P21802-11, P21802-12, P21802-13, P21802-14, P21802-15, P21802-16, P21802-17, P21802-18, P21802-19, P21802-20, P21802-21, P21802-22, and/or P21802-23), FGFR3 (e.g., UniProtKB/Swiss-Prot P22607-1 (i.e., FGFR3-IIIc), P22607-2 (i.e., FGFR3-IIIb), P22607-3, and/or P22607-4), FGFR4 (e.g., UniProtKB/Swiss-Prot P22455-1 and/or P22455-2), FGF1 (e.g., UniProtKB/Swiss-Prot P05230-1 and/or P05230-2), FGF2 (e.g., UniProtKB/Swiss-Prot P09038-1, P09038-2, P09038-3, and/or P09038-4), FGF3 (e.g., UniProtKB/Swiss-Prot P11487), FGF4 (e.g., UniProtKB/Swiss-Prot P08620), FGF5 (e.g., UniProtKB/Swiss-Prot P12034-1 and/or P12034-2), FGF6 (e.g., UniProtKB/Swiss-Prot 10767), FGF7 (e.g., UniProtKB/Swiss-Prot P21781), FGF8 (e.g., UniProtKB/Swiss-Prot P55075-1, P55075-2, P55075-3 and/or P55075-4), FGF9 (e.g., UniProtKB/Swiss-Prot P31371), FGF10 (e.g., UniProtKB/Swiss-Prot 015520), FGF11 (e.g., UniProtKB/Swiss-Prot Q92914), FGF12 (e.g., UniProtKB/Swiss-Prot P61328-1 and/or P61328-2), FGF13 (e.g., UniProtKB/Swiss-Prot Q92913-1, Q92913-2, Q92913-3, Q92913-4, and/or Q92913-5), FGF14 (e.g., UniProtKB/Swiss-Prot Q92915-1 and/or Q92915-2), FGF16 (e.g., UniProtKB/Swiss-Prot 043320), FGF17 (e.g., UniProtKB/Swiss-Prot 060258-1 and/or 060258-2), FGF18 (e.g., UniProtKB/Swiss-Prot 076093), FGF19 (e.g., UniProtKB/Swiss-Prot 095750), FGF20 (e.g., UniProtKB/Swiss-Prot Q9NP95), FGF21 (e.g., UniProtKB/Swiss-Prot Q9NSA1), FGF22 (e.g., UniProtKB/Swiss-Prot Q9HCT0), and/or FGF23 (e.g., UniProtKB/Swiss-Prot Q9GZV9).

In some embodiments of any of the methods, the antagonist of FGFR signaling is an antibody inhibitor, a small molecule inhibitor, a binding polypeptide inhibitor, and/or a polynucleotide antagonist. In some embodiments, the antagonist of FGFR signaling is a binding polypeptide inhibitor. In some embodiments, the binding polypeptide inhibitor comprises a region of the extracellular domain of FGFR linked to a Fc. In some embodiments, the antagonist of FGFR signaling is a small molecule. In some embodiments, the antagonist of FGFR signaling is an antibody.

In some embodiments of any of the methods, the antagonist of FGFR signaling is an antagonist of FGFR1 signaling. In some embodiments, the antagonist of FGFR1 signaling binds to and/or inhibits one or more of FGFR1-IIIb, FGFR1-IIIc, FGF1, FGF2, FGF3, FGF4, FGF5, FGF6, and FGF10. In some embodiments, the antagonist of FGFR1 signaling binds to and/or inhibits FGFR1 (e.g., FGFR1-IIIb and/or FGFR1-IIIc). In some embodiments, the antagonist of FGFR1 signaling binds to and/or inhibits FGF2. In some embodiments, the antagonist of FGFR1 signaling binds to and/or inhibits FGF5.

In some embodiments of any of the methods, the antagonist of FGFR1 signaling is a binding polypeptide. In some embodiments, the binding polypeptide is an FGFR1 fusion protein comprising an extracellular domain of an FGFR1 polypeptide and a fusion partner. In some embodiments, the FGFR1 is FGFR1-IIIb. In some embodiments, the FGFR1 is FGFR1-IIIb. In some embodiments, the extracellular domain comprises of amino acids 22 to 360 or 22 to 592 of FGFR1-IIIc. In some embodiments, the FGFR1 fusion protein is a protein described in U.S. Pat. No. 7,678,890, which is hereby incorporated by reference in its entirety.

In some embodiments of any of the methods, the antagonist of FGFR1 signaling is an antibody. In some embodiments, the antagonist of FGFR1 signaling is an anti-FGF2 antibody. In some embodiments, the fusion partner is an Fc polypeptide. In some embodiments, the antibody is an FGF2 antibody, for example as described in US20090304707, which is hereby incorporated by reference in its entirety, for example the antibody produced by hybridoma PTA-8864 and/or a humanized antibody thereof. In some embodiments, the antagonist of FGFR1 signaling is an anti-FGFR1 antibody. In some embodiments, the antagonist of FGFR1 signaling is an anti-FGFR1-IIIb antibody. In some embodiments, the antagonist of FGFR1 signaling is an anti-FGFR1-IIIc antibody. In some embodiments the antagonist of FGFR1 signaling is an anti-FGFR1 antibody capable of binding more than one FGFR polypeptide.

In some embodiments, the antagonist of FGFR1 signaling is a small molecule. In some embodiments, the antagonist of FGFR1 signaling is N-[2-[[4-(diethylamino)butyl]amino]-6-(3,5-dimethoxyphenyl)pyrido[2,3-d]pyrimidin-7-yl]-N'-(1,1-dimethylethyl)-urea or pharmaceutically acceptable salt thereof. In some embodiments, the antagonist of FGFR1 signaling is BGJ398 (Novartis, i.e., 3-(2,6-Dichloro-3,5-dimethoxy-phenyl)-1-{6-[4-(4-ethyl-piperazin-1-yl)-phenylamino]-pyrimidin-4-yl}-1-methyl-urea and/or a pharmaceutically acceptable salt thereof; CAS #872511-34-7). In some embodiments, the antagonist of FGFR1 signaling is AZD4547 (AstraZeneca; i.e., N-(5-(3,5-dimethoxyphenethyl)-1H-pyrazol-3-yl)-4-((3S,5R)-3,5-dimethylpiperazin-1-yl)benzamide and/or pharmaceutically acceptable salts thereof). In some embodiments, the antagonist of FGFR1 signaling is FF284 (Chugai/Debiopharm (Debio 1347).

In some embodiments of any of the methods, the antagonist of FGFR signaling is an antagonist of FGFR2 signaling. In some embodiments, the antagonist of FGFR2 signaling binds to and/or inhibits one or more of FGFR2-IIIb, FGFR2-IIIc, FGF1, FGF2, FGF3, FGF4, FGF6, FGF7, FGF9, FGF10, FGF17, FGF18 and FGF22. In some embodiments, the antagonist of FGFR2 signaling binds to and/or inhibits FGFR2 (e.g., FGFR2-IIIb and/or FGFR2-IIIc). In some embodiments, the antagonist of FGFR2 signaling binds to and/or inhibits FGF2. In some embodiments, the antagonist of FGFR2 signaling binds to and/or inhibits FGF9.

In some embodiments of any of the methods, the antagonist of FGFR2 signaling is a binding polypeptide. In some embodiments, the binding polypeptide is an FGFR2 fusion protein comprising an extracellular domain of an FGFR2 polypeptide and a fusion partner. Examples include, but are not limited to, those described in WO2008/065543 and WO2007/014123, which are incorporated by reference in their entirety. In some embodiments, the antagonist of FGFR2 signaling is an anti-FGFR2 antibody. In some embodiments, the antagonist of FGFR2 signaling is an anti-FGFR2-IIIb antibody. In some embodiments, the antagonist of FGFR2 signaling is an anti-FGFR2-IIIc antibody. In some embodiments the antagonist of FGFR2 signaling is an anti-FGFR2 antibody capable of binding more than one FGFR polypeptide. Examples of FGFR2 antibodies are known in the art and include, but are not limited to the antibodies described in U.S. Pat. No. 8,101,723, U.S. Pat. No. 8,101,721, WO2001/79266, WO2007/144893, and WO2010/054265, which are incorporated by reference in their entirety.

In some embodiments, the antagonist of FGFR2 signaling is a small molecule. In some embodiments, the antagonist of FGFR2 signaling is BGJ398 (Novartis, i.e., 3-(2,6-Dichloro-3,5-dimethoxy-phenyl)-1-{6-[4-(4-ethyl-piperazin-1-yl)-phenylamino]-pyrimidin-4-yl}-1-methyl-urea and/or a pharmaceutically acceptable salt thereof; CAS #872511-34-7). In some embodiments, the antagonist of FGFR2 signaling is AZD4547 (AstraZeneca; i.e., N-(5-(3,5-dimethoxyphenethyl)-1H-pyrazol-3-yl)-4-((3S,5R)-3,5-dimethylpiperazin-1-yl)benzamide and/or pharmaceutically acceptable salts thereof). In some embodiments, the antagonist of FGFR2 signaling is FF284 (Chugai/Debiopharm (Debio 1347).

In some embodiments of any of the methods, the antagonist of FGFR signaling is an antagonist of FGFR3 signaling. In some embodiments, the antagonist of FGFR3 signaling binds to and/or inhibits one or more of FGFR3-IIIb, FGFR3-IIIc, FGF1, FGF2, FGF4, FGF8, FGF9, FGF17, FGF18 and FGF23. In some embodiments, the antagonist of FGFR3 signaling binds to and/or inhibits FGFR3 (e.g., FGFR3-IIIb and/or FGFR3-IIIc). In some embodiments, the antagonist of FGFR3 signaling binds to and/or inhibits FGF2. In some embodiments, the antagonist of FGFR3 signaling binds to and/or inhibits FGF9.

In some embodiments of any of the methods, the antagonist of FGFR3 signaling is a binding polypeptide. In some embodiments, the binding polypeptide is an FGFR3 fusion protein comprising an extracellular domain of an FGFR3 polypeptide and a fusion partner. In some embodiments, the antagonist of FGFR3 signaling is an anti-FGFR3 antibody. In some embodiments, the antagonist of FGFR3 signaling is an anti-FGFR3-IIIb antibody. In some embodiments, the antagonist of FGFR3 signaling is an anti-FGFR3-IIIc antibody. In some embodiments the antagonist of FGFR3 signaling is an anti-FGFR3 antibody capable of binding more than one FGFR polypeptide. Examples of FGFR3 antibodies are known in the art and include, but are not limited to the antibodies described in U.S. Pat. No. 8,101,721, WO2010/111367, WO2001/79266, WO2002/102854, WO2002/10972, WO2007/144893, WO2010/002862, and/or WO2010/048026, which are incorporated by reference in their entirety.

In some embodiments, the antagonist of FGFR3 signaling is a small molecule. In some embodiments, the antagonist of FGFR3 signaling is BGJ398 (Novartis, i.e., 3-(2,6-Dichloro-3,5-dimethoxy-phenyl)-1-{6-[4-(4-ethyl-piperazin-1-yl)-phenylamino]-pyrimidin-4-yl}-1-methyl-urea and/or a pharmaceutically acceptable salt thereof; CAS #872511-34-7). In some embodiments, the antagonist of FGFR3 signaling is AZD4547 (AstraZeneca; i.e., N-(5-(3,5-dimethoxyphenethyl)-1H-pyrazol-3-yl)-4-((3S,5R)-3,5-dimethylpiperazin-1-yl)benzamide and/or pharmaceutically acceptable salts thereof). In some embodiments, the antagonist of FGFR3 signaling is FF284 (Chugai/Debiopharm (Debio 1347). In some embodiments of any of the methods, the FGFR3 antagonist is Brivanib, Dovitinib (TKI-258), and/or HM-80871A.

In some embodiments of any of the methods, the antagonist of FGFR signaling is an antagonist of FGFR4 signaling. In some embodiments, the antagonist of FGFR4 signaling binds to and/or inhibits one or more of FGFR4-IIIb, FGFR4-IIIc, FGF1, FGF2, FGF4, FGF6, FGF8, FGF9, FGF16, FGF17, FGF18, and FGF19. In some embodiments, the antagonist of FGFR4 signaling binds to and/or inhibits FGFR4 (e.g., FGFR4-IIIb and/or FGFR4-IIIc). In some embodiments, the antagonist of FGFR4 signaling binds to and/or inhibits FGF2. In some embodiments, the antagonist of FGFR4 signaling binds to and/or inhibits FGF9.

In some embodiments of any of the methods, the antagonist of FGFR4 signaling is a binding polypeptide. In some embodiments, the binding polypeptide is an FGFR4 fusion protein comprising an extracellular domain of an FGFR4 polypeptide and a fusion partner. In some embodiments, the antagonist of FGFR4 signaling is an anti-FGFR4 antibody. In some embodiments the antagonist of FGFR4 signaling is an anti-FGFR4 antibody capable of binding more than one FGFR polypeptide. Examples of FGFR4 antibodies are known in the art and include, but are not limited to the antibodies described in WO2008/052796 and WO2005/037235, which are incorporated by reference in their entirety.

In some embodiments, the antagonist of FGFR4 signaling is a small molecule. In some embodiments, a weak antagonist of FGFR4 signaling is BGJ398 (Novartis, i.e., 3-(2,6-Dichloro-3,5-dimethoxy-phenyl)-1-{6-[4-(4-ethyl-piperazin-1-yl)-phenylamino]-pyrimidin-4-yl}-1-methyl-urea and/or a pharmaceutically acceptable salt thereof; CAS #872511-34-7). In some embodiments, a weak antagonist of FGFR4 is AZD4547 (AstraZeneca; i.e., N-(5-(3,5-dimethoxyphenethyl)-1H-pyrazol-3-yl)-4-((3S,5R)-3,5-dimethylpiperazin-1-yl)benzamide and/or pharmaceutically acceptable salts thereof). In some embodiments, a weak antagonist of FGFR4 is FF284 (Chugai/Debiopharm (Debio 1347).

Exemplary FGFR antagonists are known in the art and include, but are not limited to, U.S. Pat. No. 5,288,855, U.S. Pat. No. 6,344,546, WO94/21813, US20070274981, WO2005/066211, WO2011/068893, U.S. Pat. No. 5,229,501, U.S. Pat. No. 6,656,728, U.S. Pat. No. 7,678,890, WO95/021258, U.S. Pat. No. 6,921,763, U.S. Pat. No. 6,713,474, U.S. Pat. No. 6,610,688, U.S. Pat. No. 6,297,238, US20130053376, US20130039855, US2013004492, US20120316137, US20120251538, US20120195851, US20110129524, US20110053932, US20050227921, EP1761505, WO2012/125124, WO2012/123585, WO2011/099576, WO2011/035922, WO2009148928, WO2008/149521, WO2005/079390, WO2003/080064, WO2008/075068 (in particular Example 80), WO2005/080330, which are incorporated by reference in their entirety.

In some embodiments, the antagonist of FGFR signaling may be a specific inhibitor for FGFR/FGF, for example a specific inhibitor of FGFR1. In some embodiments, the inhibitor may be a dual inhibitor or pan inhibitor wherein the antagonist of FGFR signaling inhibits FGFR/FGF and one or more other target polypeptides and/or one or more FGFRs/FGFs.

Provided here are also EGFR antagonists useful in the methods described herein. EGFR is meant the receptor tyrosine kinase polypeptide Epidermal Growth Factor Receptor which is described in Ullrich et al, Nature (1984) 309:418425, alternatively referred to as Her-1 and the c-erbB gene product, as well as variants thereof such as EGFRvIII. Variants of EGFR also include deletional, substitutional and insertional variants, for example those described in Lynch et al. (NEJM 2004, 350:2129), Paez et al. (Science 2004, 304:1497), Pao et al. (PNAS 2004, 101: 13306). In some embodiment, the EGFR is wild-type EGFR, which generally refers to a polypeptide comprising the amino acid sequence of a naturally occurring EGFR protein. In some embodiments, the EGFR antagonists are an antibody, binding polypeptide, binding small molecule, and/or polynucleotide.

Exemplary EGFR antagonists (anti-EGFR antibodies) include antibodies such as humanized monoclonal antibody known as nimotuzumab (YM Biosciences), fully human ABX-EGF (panitumumab, Abgenix Inc.) as well as fully human antibodies known as E1.1, E2.4, E2.5, E6.2, E6.4, E2.11, E6.3 and E7.6.3 and described in U.S. Pat. No. 6,235,883; MDX-447 (Medarex Inc). Pertuzumab (2C4) is a humanized antibody that binds directly to HER2 but interferes with HER2-EGFR dimerization thereby inhibiting EGFR signaling. Other examples of antibodies which bind to EGFR include GA201 (RG7160; Roche Glycart AG), MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., *J. Biol. Chem.* 279 (29):30375-30384 (2004)). The anti-EGFR antibody may be conjugated with a cytotoxic agent, thus generating an immunoconjugate (see, e.g., EP659,439A2, Merck Patent GmbH). In some embodiments, the anti-EGFR antibody is cetuximab. In some embodiments, the anti-EGFR antibody is panitumumab. In some embodiments, the anti-EGFR antibody is zalutumumab, nimotuzumab, and/or matuzumab.

Anti-EGFR antibodies that are useful in the methods include any antibody that binds with sufficient affinity and specificity to EGFR and can reduce or inhibit EGFR activity. The antibody selected will normally have a sufficiently strong binding affinity for EGFR, for example, the antibody may bind human c-met with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g., RIA's), for example. Preferably, the anti-EGFR antibody of the invention can be used as a therapeutic agent in targeting and interfering with diseases or conditions wherein EGFR/EGFR ligand activity is involved. Also, the antibody may be subjected to other biological activity assays, e.g., in order to evaluate its effectiveness as a therapeutic. Such assays are known in the art and depend on the target antigen and intended use for the antibody. In some embodiments, a EGFR arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the EGFR-expressing cell. Bispecific antibodies may also be used to localize cytotoxic agents to cells which express EGFR. These antibodies possess an EGFR-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

Exemplary EGFR antagonists also include small molecules such as compounds described in U.S. Pat. No. 5,616,582, U.S. Pat. No. 5,457,105, U.S. Pat. No. 5,475,001, U.S. Pat. No. 5,654,307, U.S. Pat. No. 5,679,683, U.S. Pat. No. 6,084,095, U.S. Pat. No. 6,265,410, U.S. Pat. No. 6,455,534, U.S. Pat. No. 6,521,620, U.S. Pat. No. 6,596,726, U.S. Pat. No. 6,713,484, U.S. Pat. No. 5,770,599, U.S. Pat. No. 6,140,332, U.S. Pat. No. 5,866,572, U.S. Pat. No. 6,399,602, U.S. Pat. No. 6,344,459, U.S. Pat. No. 6,602,863, U.S. Pat. No. 6,391,874, WO9814451, WO9850038, WO9909016, WO9924037, WO9935146, WO00132651, U.S. Pat. No. 6,344,455, U.S. Pat. No. 5,760,041, U.S. Pat. No. 6,002,008, and/or U.S. Pat. No. 5,747,498. Particular small molecule EGFR antagonists include OSI-774 (CP-358774, erlotinib, OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); Iressa® (ZD1839, gefitinib, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide); lapatinib (Tykerb, GlaxoSmithKline); ZD6474 (Zactima, AstraZeneca); CUDC-101 (Curis); canertinib (CI-1033); AEE788 (6-[4-[(4-ethyl-1-piperazinyl)methyl]phenyl]-N-[(1R)-1-phenylethyl]-7H-pyrrolo[2,3-d]pyrimidin-4-amine, WO2003013541, Novartis) and PKI166 4-[4-[[(1R)-1-phenylethyl]amino]-7H-pyrrolo[2,3-d]pyrimidin-6-yl]-phenol, WO9702266 Novartis). In some embodiments, the EGFR antagonist is N-(3-ethynylphenyl)-6,7-bis(2-methoxyethoxy)-4-quinazolinamine and/or a pharmaceutical acceptable salt thereof (e.g., N-(3-ethynylphenyl)-6,7-bis(2-methoxyethoxy)-4-quinazolinamine-HCl). In some embodiments, the EGFR antagonist is gefitinib and/or a pharmaceutical acceptable salt thereof. In some embodiments, the EGFR antagonist is lapatinib and/or a pharmaceutical acceptable salt thereof. In some embodiments, the EGFR antagonist is gefitinib and/or erlotinib.

In some embodiments, the EGFR antagonist may be a specific inhibitor for EGFR. In some embodiments, the inhibitor may be a dual inhibitor or pan inhibitor wherein the EGFR antagonist inhibits EGFR and one or more other target polypeptides.

A. Antibodies

Provided herein isolated antibodies that bind to a polypeptide of interest, such as an FGFR (e.g., FGFR1, FGFR2, FGFR3, and/or FGFR4), FGF (e.g., FGF1-23), and/or EGFR for use in the methods described herein. In any of the above embodiments, an antibody is humanized. Further, the antibody according to any of the above embodiments is a monoclonal antibody, including a chimeric, humanized or human antibody. In one embodiment, the antibody is an antibody fragment, e.g., a Fv, Fab, Fab', scFv, diabody, or F(ab')$_2$ fragment. In another embodiment, the antibody is a full length antibody, e.g., an "intact IgG1" antibody or other antibody class or isotype as defined herein.

In a further aspect, an antibody according to any of the above embodiments may incorporate any of the features, singly or in combination, as described in Sections below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In one embodiment, Kd is measured by a radiolabeled antigen binding assay (RIA). In one embodiment, the RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity-determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing Veloci-Mouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., Monoclonal Antibody Production Techniques and Applications, pp. 51-63 (Marcel Dekker, Inc., New York, 1987); and Boemer et al., *J. Immunol.,* 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Hist. & Histopath.,* 20(3):927-937 (2005) and Vollmers and Brandlein, *Methods Find Exp. Clin. Pharmacol.,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. *Methods Mol. Biol.* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, *Methods Mol. Biol.* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227:

381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is a polypeptide of interest, such as FGFR (e.g., FGFR1, FGFR2, FGFR3, and/or FGFR4), FGF (e.g., FGF1-23), and/or EGFR and the other is for any other antigen. In certain embodiments, bispecific antibodies may bind to two different epitopes of a polypeptide of interest, such as FGFR/FGF and/or EGFR. Bispecific antibodies may also be used to localize cytotoxic agents to cells which express a polypeptide of interest, such as FGFR (e.g., FGFR1, FGFR2, FGFR3, and/or FGFR4), FGF (e.g., FGF1-23), and/or EGFR. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to a polypeptide of interest, such as FGFR (e.g., FGFR1, FGFR2, FGFR3, and/or FGFR4), FGF (e.g., FGF1-23), and/or EGFR as well as another, different antigen (see, US 2008/0069820, for example).

7. Antibody Variants a) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express Fc (RI, Fc (RII and Fc (RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821, 337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).) In certain embodiments, an antibody variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. No. 5,648,260; U.S. Pat. No. 5,624,821; and WO 94/29351 concerning other examples of Fc region variants.

c) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

B. Immunoconjugates

Further provided herein are immunoconjugates comprising antibodies which bind a polypeptide of interest such as FGFR (e.g., FGFR1, FGFR2, FGFR3, and/or FGFR4), FGF (e.g., FGF1-23), or EGFR, conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes for use in the methods described herein.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

C. Binding Polypeptides

Binding polypeptides are polypeptides that bind, preferably specifically, to FGFR (e.g., FGFR1, FGFR2, FGFR3, and/or FGFR4), FGF (e.g., FGF1-23), and/or EGFR are also provided for use in the methods described herein. In some embodiments, the binding polypeptides are FGFR (e.g., FGFR1, FGFR2, FGFR3, and/or FGFR4) and/or FGF (e.g., FGF1-23) antagonists and/or EGFR antagonists. Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding, preferably specifically, to a target, e.g., FGFR (e.g., FGFR1, FGFR2, FGFR3, and/or FGFR4), FGF (e.g., FGF1-23), or EGFR, as described herein. Binding polypeptides may be identified without undue experimentation using well known techniques. In this regard, it is noted that techniques for screening polypeptide libraries for binding polypeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth*, 102:259-274 (1987); Schoofs et al., *J. Immunol*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

D. Binding Small Molecules

Provided herein are binding small molecules for use as a small molecule antagonist of FGFR (e.g., FGFR1, FGFR2, FGFR3, and/or FGFR4), FGF (e.g., FGF1-23), and/or EGFR for use in the methods described above.

Binding small molecules are preferably organic molecules other than binding polypeptides or antibodies as defined herein that bind, preferably specifically, to FGFR (e.g., FGFR1, FGFR2, FGFR3, and/or FGFR4), FGF (e.g., FGF1-23), and/or EGFR as described herein. Binding organic small molecules may be identified and chemically synthesized using known methodology (see, e.g., PCT Publication Nos. WO00/00823 and WO00/39585). Binding organic small molecules are usually less than about 2000 daltons in size, alternatively less than about 1500, 750, 500, 250 or 200 daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide of interest are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

E. Antagonist Polynucleotides

Provided herein are also polynucleotide antagonists for use in the methods described herein. The polynucleotide may be an antisense nucleic acid and/or a ribozyme. The antisense nucleic acids comprise a sequence complementary to at least a portion of an RNA transcript of a gene of interest, such as FGFR (e.g., FGFR1, FGFR2, FGFR3, and/or FGFR4), FGF (e.g., FGF1-23), and/or EGFR gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double stranded antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, *Nature* 372:333-335. Thus, oligonucleotides complementary to either the 5'- or 3'-non-translated, non-coding regions of the gene, could be used in an antisense approach to inhibit translation of endogenous mRNA. Polynucleotides complementary to the 5' untranslated region of the mRNA should include the complement of the AUG start codon. Antisense polynucleotides complementary to mRNA coding regions are less efficient inhibitors of translation but could be used in accordance with the invention. Whether designed to hybridize to the 5'-, 3'- or coding region of an mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

F. Antibody and Binding Polypeptide Variants

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into and/or substitutions of residues within the amino acid sequences of the antibody and/or binding polypeptide. Any combination of deletion, insertion, and substitution can be made to arrive at the final construct, provided that the final construct possesses the desired characteristics, e.g., antigen-binding.

In certain embodiments, antibody variants and/or binding polypeptide variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody and/or binding polypeptide of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

G. Antibody and Binding Polypeptide Derivatives

In certain embodiments, an antibody and/or binding polypeptide provided herein may be further modified to contain additional nonproteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions, etc.

In another embodiment, conjugates of an antibody and/or binding polypeptide to nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody and/or binding polypeptide-nonproteinaceous moiety are killed.

IV. Methods of Screening and/or Identifying Antagonists of FGFR Signaling with Desired Function Additional antagonists of a polypeptide of interest, such as FGFR (e.g., FGFR1, FGFR2, FGFR3, and/or FGFR4), FGF (e.g., FGF1-23), and/or EGFR for use in the methods described herein, including antibodies, binding polypeptides, and/or small molecules have been described above. Additional antagonists of such as antibodies, binding polypeptides, and/or binding small molecules provided herein may be identified, screened for, or characterized for their physical/chemical properties and/or biological activities by various assays known in the art.

In certain embodiments, a computer system comprising a memory comprising atomic coordinates of FGFR (e.g., FGFR1, FGFR2, FGFR3, and/or FGFR4) and/or FGF (e.g., FGF1-23), polypeptide are useful as models for rationally identifying compounds that a ligand binding site of FGFR signaling. Such compounds may be designed either de novo, or by modification of a known compound, for example. In other cases, binding compounds may be identified by testing known compounds to determine if the "dock" with a molecular model of FGFR (e.g., FGFR1, FGFR2, FGFR3, and/or FGFR4) and/or FGF (e.g., FGF1-23). Such docking methods are generally well known in the art.

FGFR signaling crystal structure data can be used in conjunction with computer-modeling techniques to develop models of binding of various FGFR (e.g., FGFR1, FGFR2, FGFR3, and/or FGFR4) and/or FGF (e.g., FGF1-23)-binding compounds by analysis of the crystal structure data. The site models characterize the three-dimensional topography of site surface, as well as factors including van der Waals contacts, electrostatic interactions, and hydrogen-bonding opportunities. Computer simulation techniques are then used to map interaction positions for functional groups including but not limited to protons, hydroxyl groups, amine groups, divalent cations, aromatic and aliphatic functional groups, amide groups, alcohol groups, etc. that are designed to interact with the model site. These groups may be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although in general, pharmacophores interact with a site through non-covalent mechanisms.

The ability of a pharmacophore or candidate compound to bind to FGFR (e.g., FGFR1, FGFR2, FGFR3, and/or FGFR4) and/or FGF (e.g., FGF1-23) polypeptide can be analyzed in addition to actual synthesis using computer modeling techniques. Only those candidates that are indicated by computer modeling to bind the target (e.g., FGFR (e.g., FGFR1, FGFR2, FGFR3, and/or FGFR4) and/or FGF (e.g., FGF1-23) polypeptide binding site) with sufficient binding energy (in one example, binding energy corresponding to a dissociation constant with the target on the order of $10^{-2}$ M or tighter) may be synthesized and tested for their ability to bind to FGFR (e.g., FGFR1, FGFR2, FGFR3, and/or FGFR4) and/or FGF (e.g., FGF1-23), polypeptide and to inhibit FGFR signaling, if applicable, enzymatic function using enzyme assays known to those of skill in the art and/or as described herein. The computational evaluation step thus avoids the unnecessary synthesis of compounds that are unlikely to bind FGFR (e.g., FGFR1, FGFR2, FGFR3, and/or FGFR4) and/or FGF (e.g., FGF1-23) polypeptide with adequate affinity.

FGFR signaling pharmacophore or candidate compound may be computationally evaluated and designed by means of a series of steps in which chemical entities or fragments are screened and selected for their ability to associate with individual binding target sites on FGFR (e.g., FGFR1, FGFR2, FGFR3, and/or FGFR4) and/or FGF (e.g., FGF1-23) polypeptide. One skilled in the art may use one of several methods to screen chemical entities or fragments for their ability to associate with FGFR (e.g., FGFR1, FGFR2, FGFR3, and/or FGFR4) and/or FGF (e.g., FGF1-23) polypeptide, and more particularly with target sites on FGFR (e.g., FGFR1, FGFR2, FGFR3, and/or FGFR4) and/or FGF (e.g., FGF1-23) polypeptide. The process may begin by visual inspection of, for example a target site on a computer screen, based on FGFR (e.g., FGFR1, FGFR2, FGFR3, and/or FGFR4) and/or FGF (e.g., FGF1-23) polypeptide coordinates, or a subset of those coordinates known in the art.

To select for an antagonist which induces cancer cell death, loss of membrane integrity as indicated by, e.g., propidium iodide (PI), trypan blue or 7AAD uptake may be assessed relative to a reference. A PI uptake assay can be performed in the absence of complement and immune effector cells. A tumor cells are incubated with medium alone or medium containing the appropriate combination therapy. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 pig/ml). Samples may be analyzed using a FACSCAN® flow cytometer and FACSCONVERT® CellQuest software (Becton Dickinson). Those antagonists that induce statistically significant levels of cell death compared to media alone and/or monotherapy as determined by PI uptake may be selected as cell death-inducing antibodies, binding polypeptides or binding small molecules.

In some embodiments of any of the methods of screening and/or identifying, the candidate antagonist of FGFR (e.g., FGFR1, FGFR2, FGFR3, and/or FGFR4) and/or FGF (e.g., FGF1-23) is an antibody, binding polypeptide, binding small molecule, or polynucleotide. In some embodiments, the antagonist of FGFR (e.g., FGFR1, FGFR2, FGFR3, and/or FGFR4) and/or FGF (e.g., FGF1-23) is an antibody. In some embodiments, the antagonist of FGFR (e.g., FGFR1, FGFR2, FGFR3, and/or FGFR4) and/or FGF (e.g., FGF1-23) is a small molecule.

V. Pharmaceutical Formulations

Pharmaceutical formulations of an antagonist of FGFR signaling and an EGFR antagonist as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. In some embodiments, the antagonist of FGFR signaling and/or EGFR antagonist is a binding small molecule, an antibody, binding polypeptide, and/or polynucleotide. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antagonist of FGFR signaling and an EGFR antagonist, which matrices are in the form of shaped articles, e.g., films, or microcapsules.

The formulations to be used for in vivo administration are generally sterile. Sterility may be readily accomplished, e.g., by filtration through sterile filtration membranes.

VI. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antagonist of FGFR signaling and an EGFR antagonist described herein. The label or package insert indicates that the composition is used for treating the condition of choice. Moreover, the article of manufacture may comprise (a) a first container with a composition contained therein, wherein the composition comprises an antagonist of FGFR signaling and an EGFR antagonist; and (b) a second container with a composition contained therein, wherein the composition comprises a further cytotoxic or otherwise therapeutic agent.

In some embodiments, the article of manufacture comprises a container, a label on said container, and a composition contained within said container; wherein the composition includes one or more reagents (e.g., primary antibodies that bind to one or more biomarkers or probes and/or primers to one or more of the biomarkers described herein), the label on the container indicating that the composition can be used to evaluate the presence of one or more biomarkers in a sample, and instructions for using the reagents for evaluating the presence of one or more biomarkers in a sample. The article of manufacture can further comprise a set of instructions and materials for preparing the sample and utilizing the reagents. In some embodiments, the article of manufacture may include reagents such as both a primary and secondary antibody, wherein the secondary antibody is conjugated to a label, e.g., an enzymatic label. In some embodiments, the article of manufacture one or more probes and/or primers to one or more of the biomarkers described herein.

In some embodiments of any of the article of manufacture, the antagonist of FGFR signaling and/or an EGFR antagonist is an antibody, binding polypeptide, binding small molecule, or polynucleotide. In some embodiments, the antagonist of FGFR signaling and/or EGFR antagonist is a small molecule. In some embodiments, the antagonist of FGFR signaling and/or EGFR antagonist is an antibody. In some embodiments, the antibody is a monoclonal antibody. In some embodiments, the antibody is a human, humanized, or chimeric antibody. In some embodiments, the antibody is an antibody fragment and the antibody fragment binds FGFR signaling and/or inhibitor.

The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Other optional components in the article of manufacture include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

It is understood that any of the above articles of manufacture may include an immunoconjugate described herein in place of or in addition to an antagonist of FGFR signaling and an EGFR antagonist.

EXAMPLES

The following are examples of methods and compositions of the invention. It is understood that various other embodiments may be practiced, given the general description provided above.

Example 1

Two models of acquired resistance to erlotinib were identified that were associated with an EMT phenotype and a dependence on autocrine FGF-FGFR signaling for resistance. Evidence for FGFR pathway activation in the erlotinib-resistant cell population included an increase in FGF2, FGFR1 and phospho-FRS2. Inhibition of FGFR signaling using a small molecule kinase inhibitor or FGFR1-Fc neutralization of FGFR1 ligands re-sensitized resistant cells to erlotinib. Re-sensitization was accompanied by an inhibition of downstream signaling. In contrast, inhibition of AXL, a kinase that was recently been identified as an EMT-associated driver of erlotinib resistance in some pre-clinical models, failed to re-sensitize erlotinib-resistant cells. These findings were consistent with autocrine FGFR pathway activation, as FGF ligand neutralization in the absence of an exogenous source of ligand can re-sensitize cells to erlotinib. Finally, FGFR pathway inhibition suppressed the development of resistance to erlotinib in sensitive parental cells. These data indicated that FGFR activation serves as a mechanism of acquired resistance to erlotinib in cases associated with an EMT and that combined inhibition of EGFR and FGFR signaling could be beneficial in treating such cases.

Materials and Methods
  Cell Culture
  All cells are maintained in RPMI media (high glucose) supplemented with 5% Fetal Bovine Serum (FBS) and L-glutamine under 5% $CO_2$ at 37° C.
  Cell Viability Assays
  $10^3$ cells were plated in each well of 384-well plate. 24 hours after plating, added indicated concentration drug to each well. 72 hours after dosing, added CellTiter-Glo Reagent (CellTiter Glo Luminescent Cell Viability Assay, Promega) to each well, incubate the plate at room temperature for 10 minutes, record luminescence by EnVision 2101 Multilabel Reader (PerkinElmer).

Annexin V Assay
  $5\times10^4$ cells were plated in 10 $cm^2$ plate. 24 hours after plating, media was removed and replaced with media containing indicated concentration drug for 72 hours. Cells were harvested and stained with annexin V and PI (FITC Annexin V Apoptosis Detection Kit, BD Biosciences). Cells were analyzed by FACScalibur (BD Biosciences).

Scratch Wound Assay
  Coated Essen Image Lock plate with 20 ug/ml collage I for 30 minutes at room temperature, removed collage I and washed with Phosphate Buffered Saline (PBS). $6\times10^4$ cells were plated in each well. 24 hours after plating, scratched the wells by using 96-well WoundMaker (ESSEN Bioscience). After wounding, aspirate the media from each well and wash each well two times with PBS. After washing, media were added and the plate was placed inside the IncuCyte (IncuCyte FLR, ESSEN Bioscience). Wound images were taken at 2 hours intervals for 48 hours. The data was analyzed by Relative Wound Density.

Cellular Invasion Assay
  $1.25\times10^4$ cells in 0.1% BSA RPMI1640 media were plated in top well of BD Insert Hts 96W plate 8UM. Added 200 µl of indicated condition media in the bottom well. 16 hours after plating, removed the media from top and bottom well. Fixed cells with cold methanol in bottom well for 30 minutes at 4° C. Aspirated methanol, let plate dry at room temperature and then stained with YO-PRO (Life technologies) for 10 minutes. Washed with PBS for two times. Fluorescence quantitation was carried out at 485/538 nm with SpectraMax M5 (Molecular Devices).

Clonogenic Assay
  $10^5$ cells were plated in 10 $cm^2$ plate. 24 hours after plating, media was removed and replaced with media containing indicated drugs. Fresh media was replaced every 3 to 4 days until cells reached confluence (4 weeks) or 6 weeks to stop culture. Media was removed, cells were washed with PBS, then stained with 0.5% crystal violet for 20 minutes at room temperature. Dye was removed, cell monolayers were washed with water, dry the plate and take a picture as record.

Generation of Erlotinib Resistant Lines
  Drug-sensitive cells (HCC4006 and HCC827) were treated with 2 uM erlotinib for 2 months. Fresh media containing 2 uM erlotinib were replaced every 3 to 4 days. Viable cells were collected as erlotinib-resistant cells.

Figure 1C:
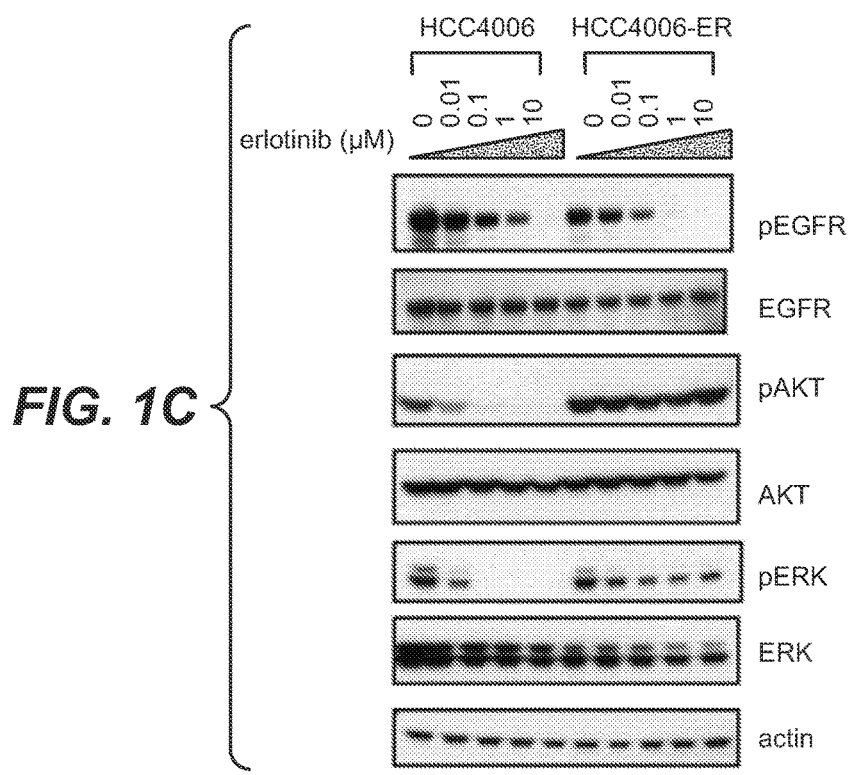
Figure 1B:
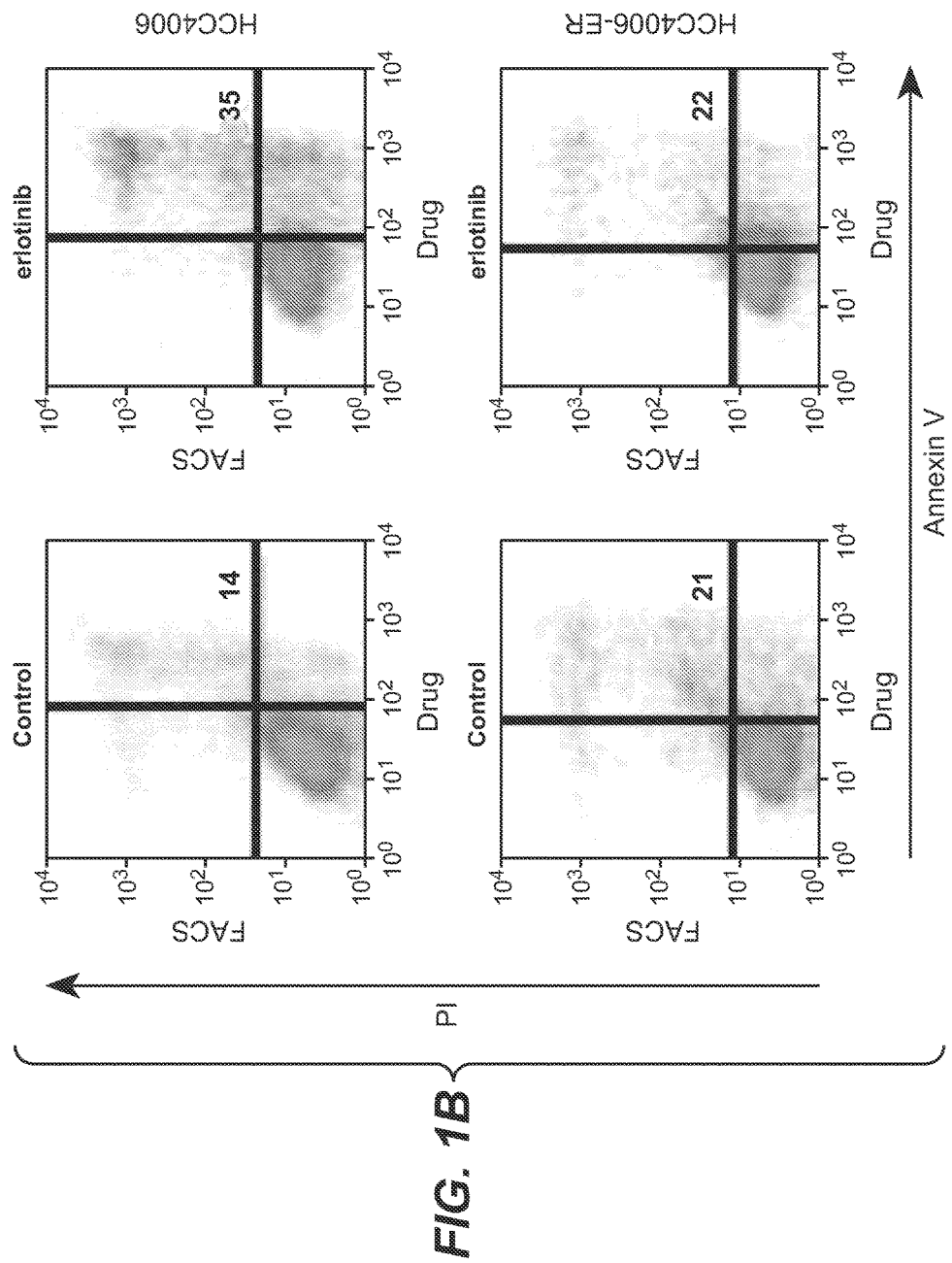
Figure 2A:
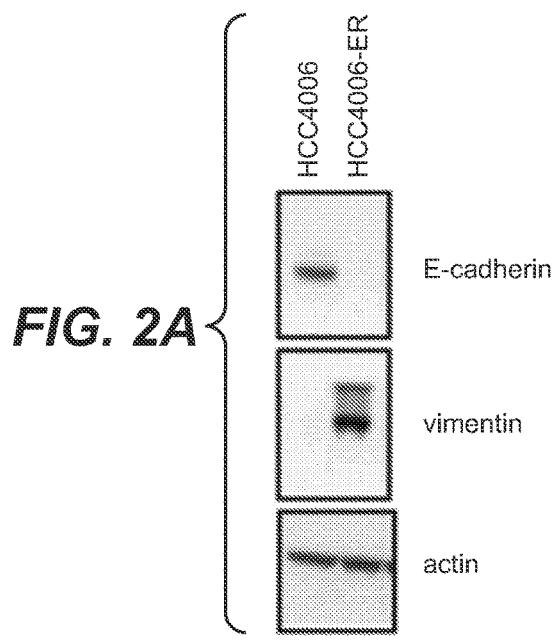
FIG. 2A-D. | HCC4006-ER cells exhibit features of EMT. A, Parental and erlotinib-resistant HCC4006 cell lysates were immunoblotted for the epithelial-associated and mesenchymal-associated proteins, E-cadherin, and vimentin, respectively. B, Migratory rate of HCC4006 and HCC4006-ER cells were measured in a scratch wound assay and wound closure was monitored by imaginon Incucyte. C, Cellular invasion was measured in a transwell assay in the presence of 1% or 10% fetal bovine serum (FBS). D, Cell viability of HCC4006 and HCC4006-ER cells were measured at the indicated time points.
Figure 2B:
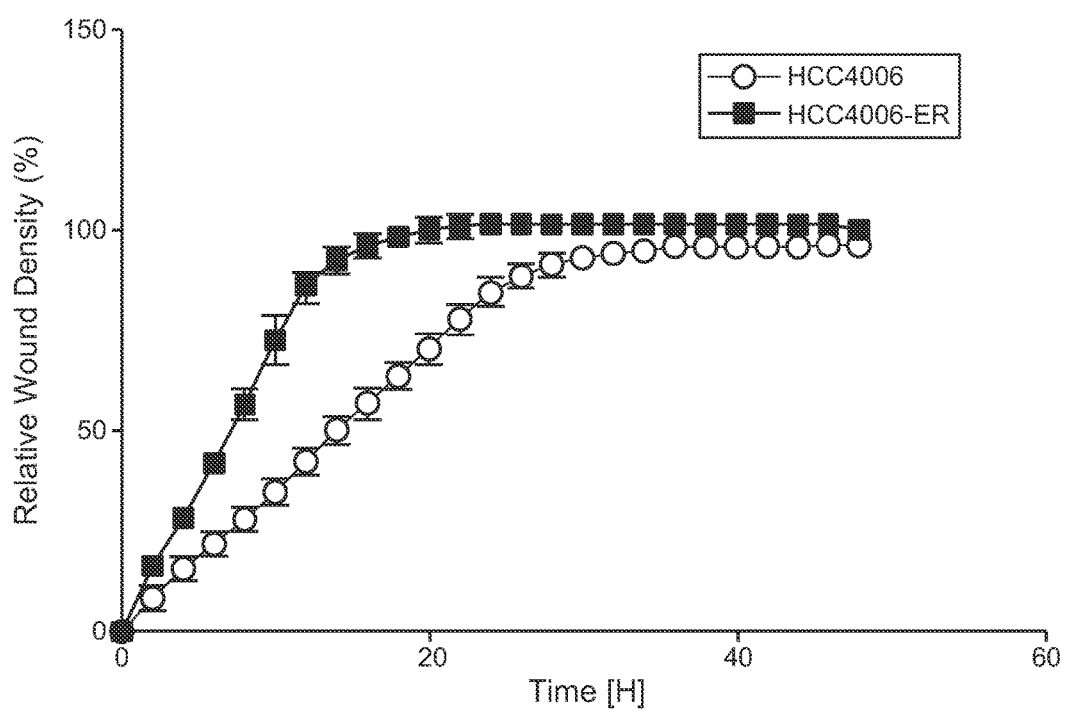
Figure 2C:
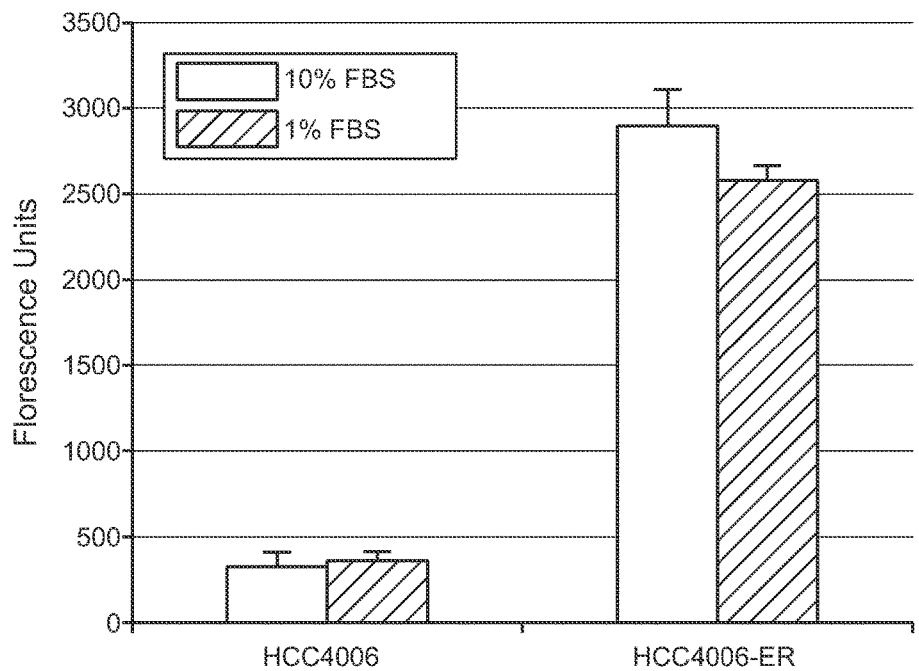
Figure 2D:
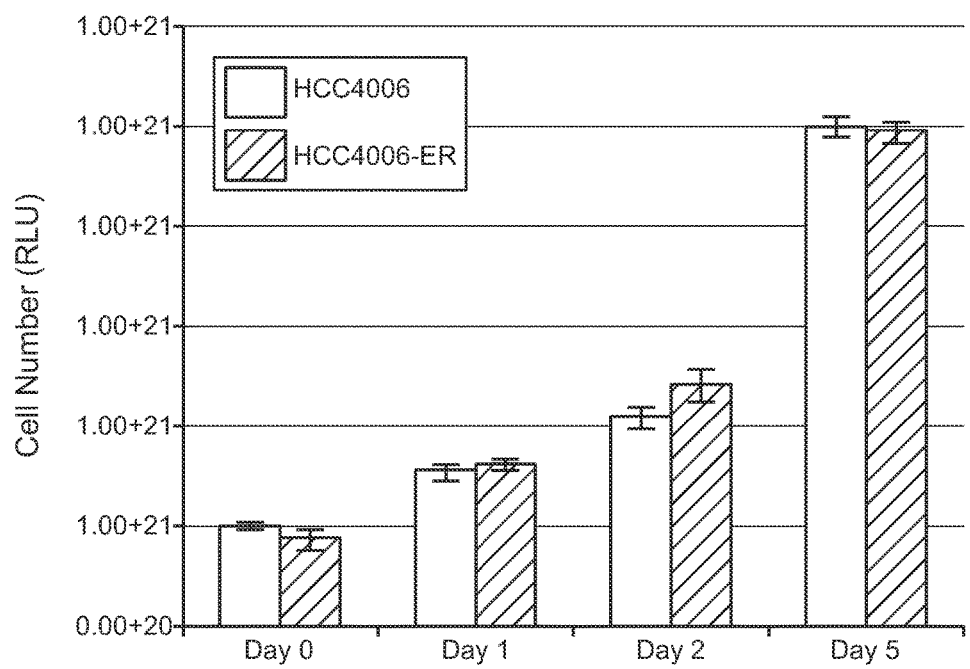
Figure 3A:
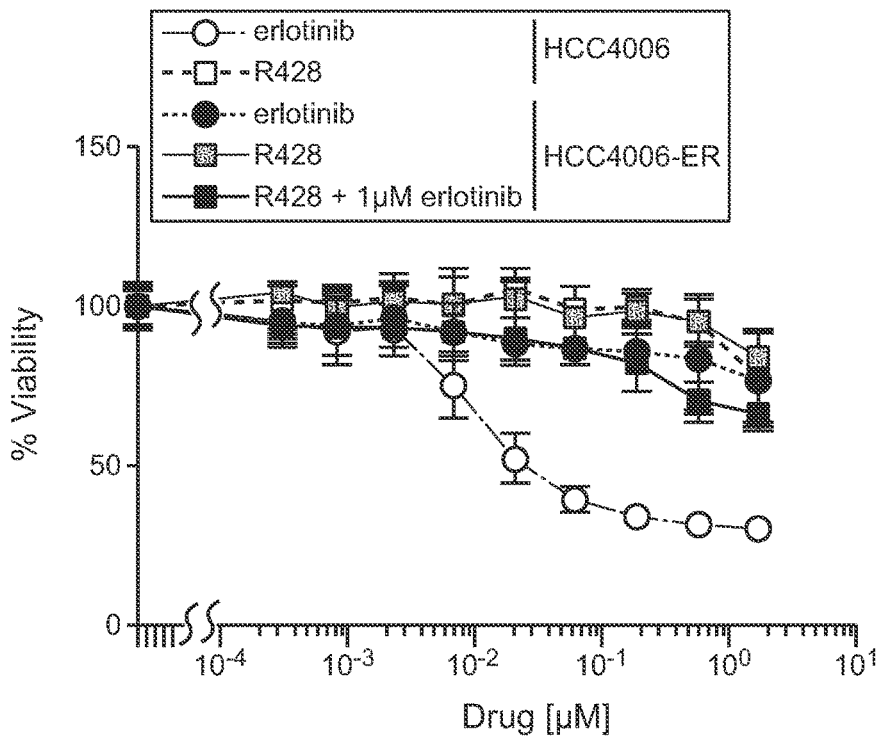
FIG. 3A-C. | AXL inhibition cannot overcome resistance to erlotinib in HCC4006-ER cells. A, Cell viability of parental and erlotinib-resistant HCC4006 cells was measured following 72 h culture in the presence of the indicated concentration of the AXL kinase inhibitor, R428, and/or erlotinib. B, Cell viability of erlotinib-resistant HCC4006-ER cells was measured in the presence of the indicated concentrations of erlotinib following the siRNA-mediated knockdown of AXL or control siRNA. C, Immunoblot controls demonstrating the effect of siRNAs targeting AXL on AXL expression levels.
Figure 3B:
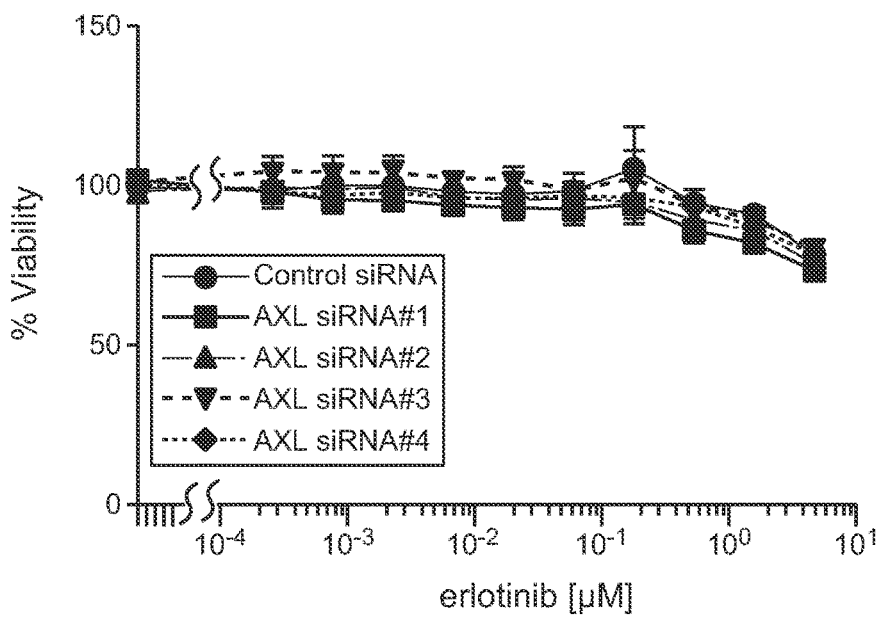
Figures 3C, 4A:
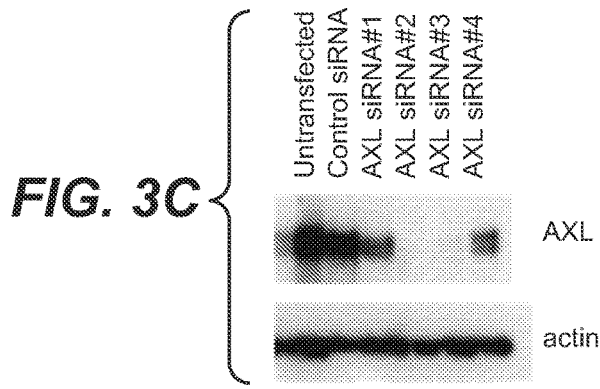
FIG. 4A-C. | FGFR1 and specific FGF ligands were significantly elevated in HCC4006-ER cells. A, Fold change (log) in gene expression for FGF family receptors and ligands in HCC4006-ER compared to HCC4006 cells, based upon microarray profiling. B, Confirmation of select genes by qRT-PCR. C, FGF2 protein levels are increased in both the supernatant and lysates of HCC4006-ER cells as detected by ELISA.

Results
  As shown in FIG. 1A-C, HCC4006-ER cells are resistant to erlotinib. In addition to being resistant to erlotinib, HCC4006-ER cells exhibit features of EMT as shown in FIG. 2A-D. HCC4006 express epithelial-associated proteins such as E-cadherin while HCC4006 erlotinib-resistant cells express mesenchymal-associated proteins, vimentin. Further, migratory rate of HCC4006 and HCC4006-ER cells were measured in a scratch wound assay and wound closure, cellular invasion, and cell viability of HCC4006 and HCC4006-ER cells were measured. There was a striking difference in cellular invasion capabilities between HCC4006 and HCC4006-ER cells, while there was no significant difference in overall viability between the parental and resistant to erlotinib cells. As shown in FIG. 3A-C by use of the AXL kinase inhibitor (R428) and siRNA-mediated knockdown, AXL inhibition cannot overcome resistance to erlotinib in HCC4006-ER cells.

Figure 4B:
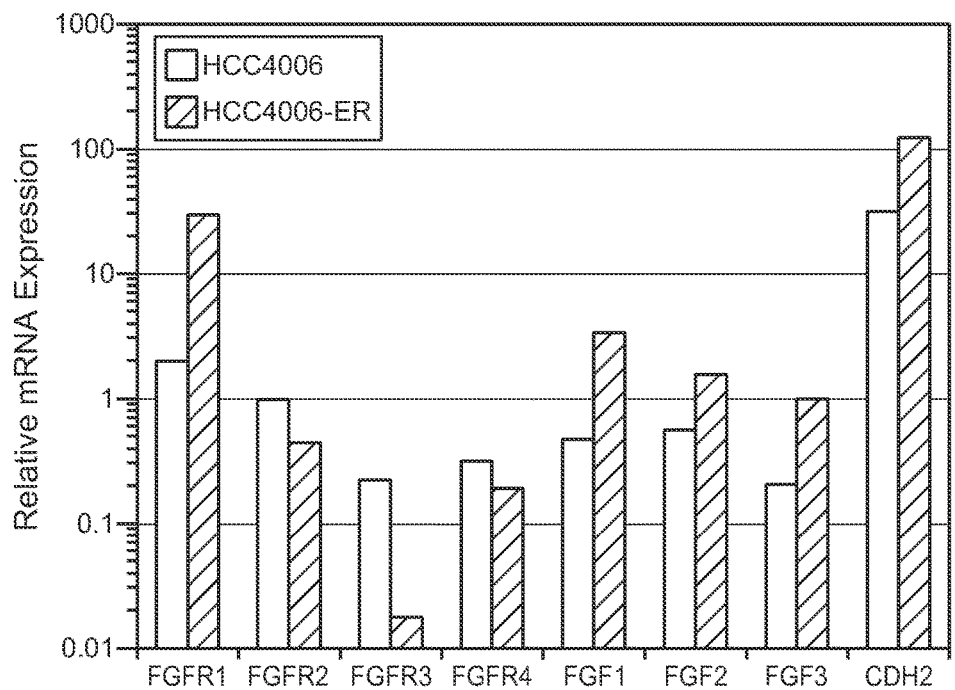
Figure 4C:
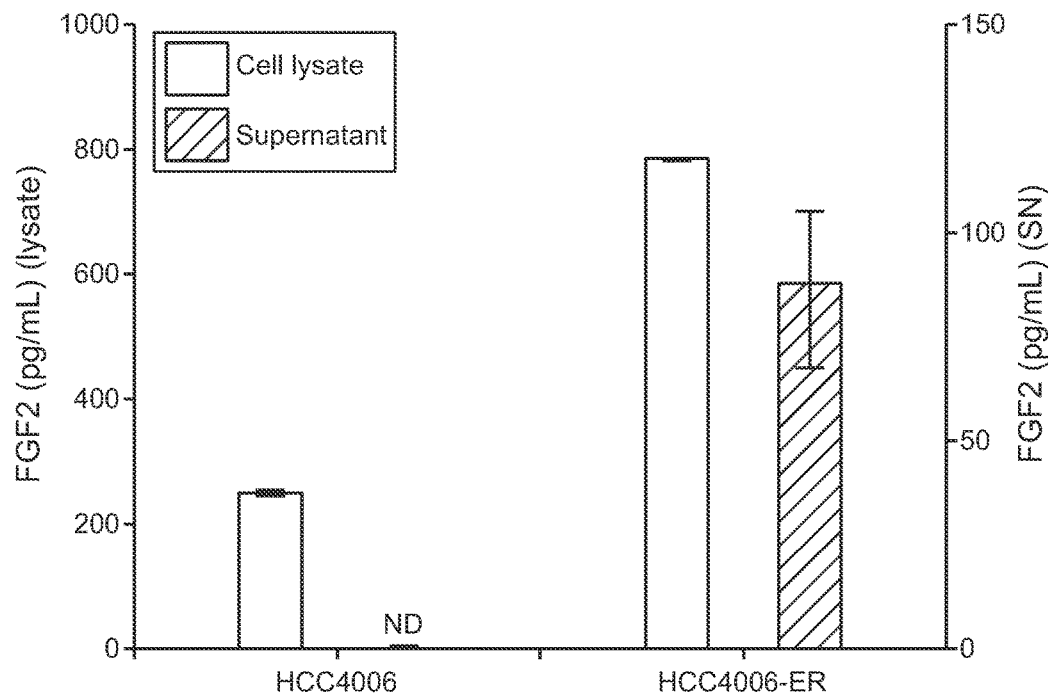
Figure 5A:
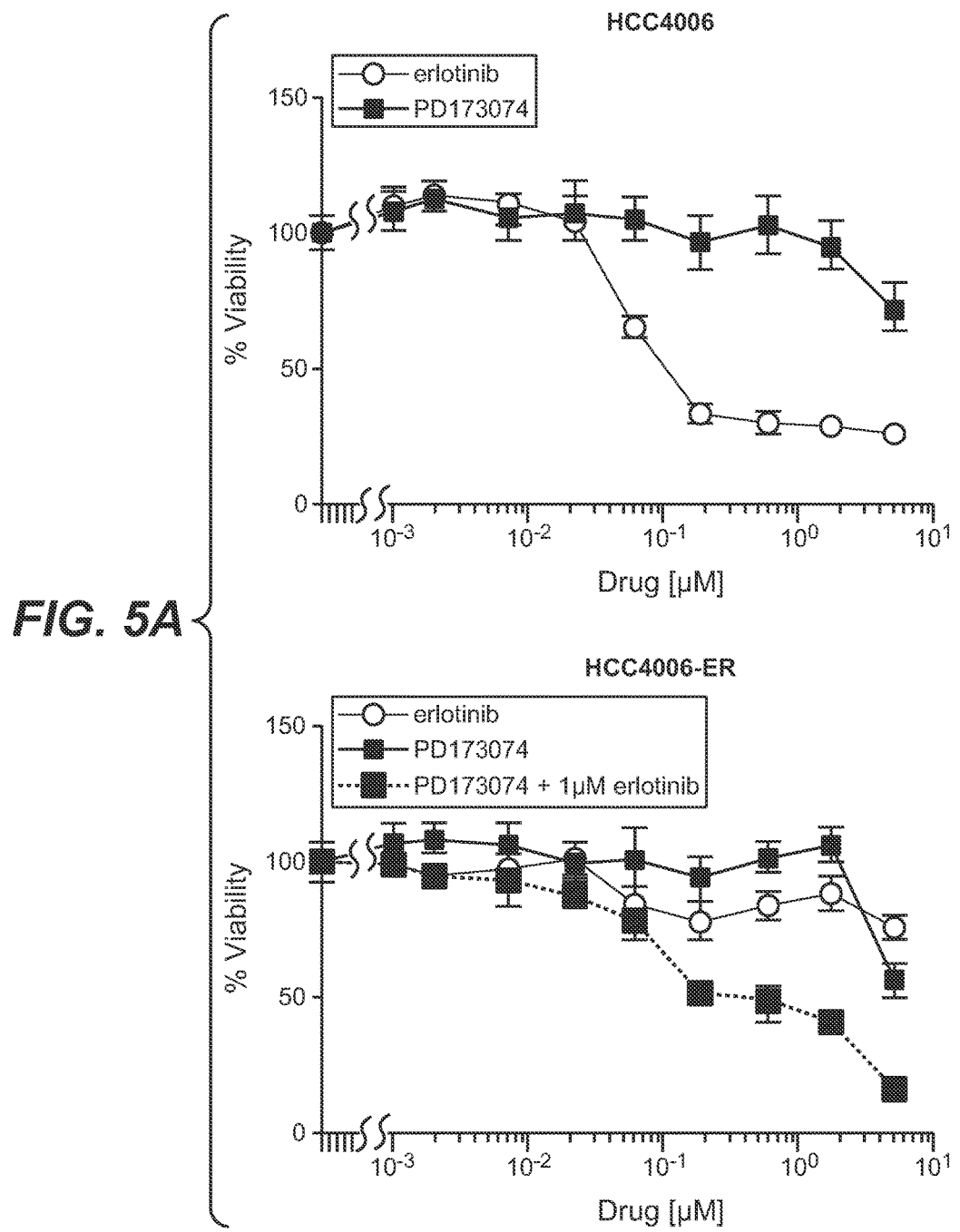
FIG. 5A-C. | Specific inhibition of ligand-dependent FGFR signalling overcame resistance to erlotinib in HCC4006-ER cells. A, Cell viability in HCC4006 (left) and HCC4006-ER (right) cells was assayed at 72 h in the presence of the indicated concentrations of erlotinib or PD173074. B, HCC4006 and HCC4006-ER cells were treated with the indicated drugs for 2 h and cell lysates were immunoblotted with the indicated antibodies. Stimulation of cells with exogenous FGF2+heparin served as a positive control for FGFR activation. C, Cell viability in HCC4006 and HCC4006-ER cells following treatment for 72 h in the presence of recombinant soluble FGFR-Fc to neutralize FGF ligands and controls.
Figure 5B:
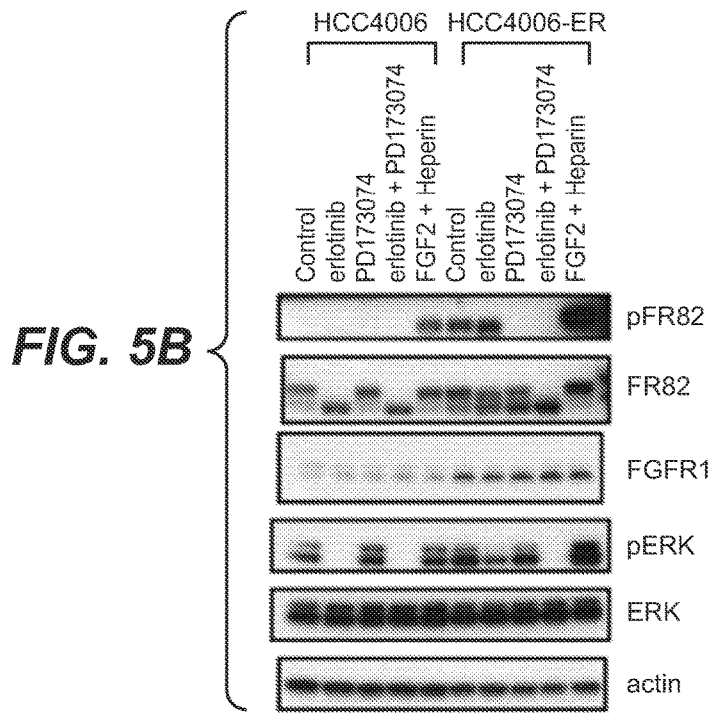
Figure 5C:
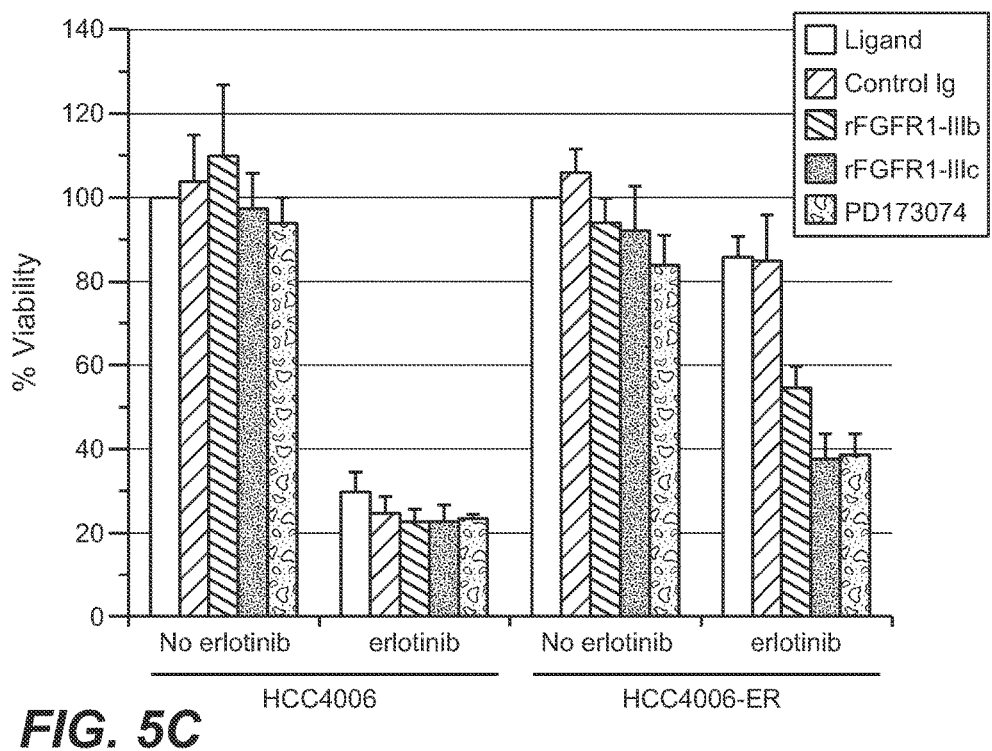
Figure 6:
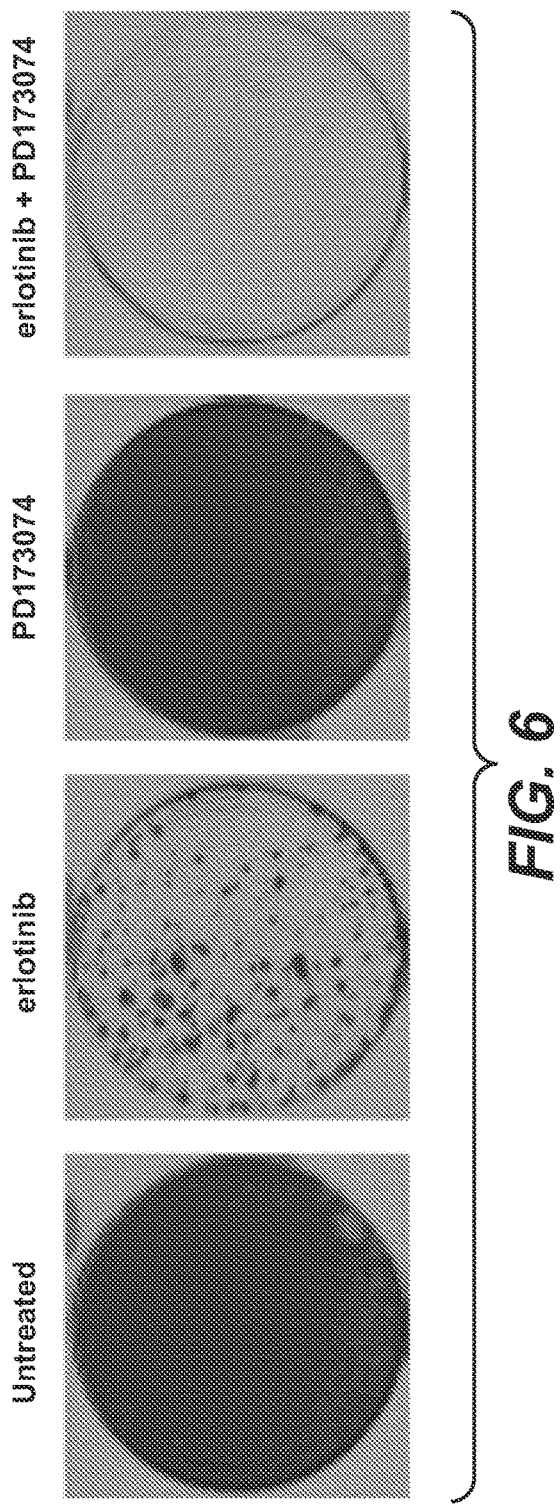
FIG. 6 | FGFR inhibition suppressed the development of resistance to erlotinib in HCC4006 cells. Cells ($1 \times 10^5$) were treated continuously with erlotinib (1 µM), PD173074 (0.5 µM) or the combination prior to fixation and staining with crystal violet. Untreated and PD173074-treated cultures were stained as 4 weeks, whereas erlotinib and combination-treated cultures were stained at 6 weeks.
Figure 7A:
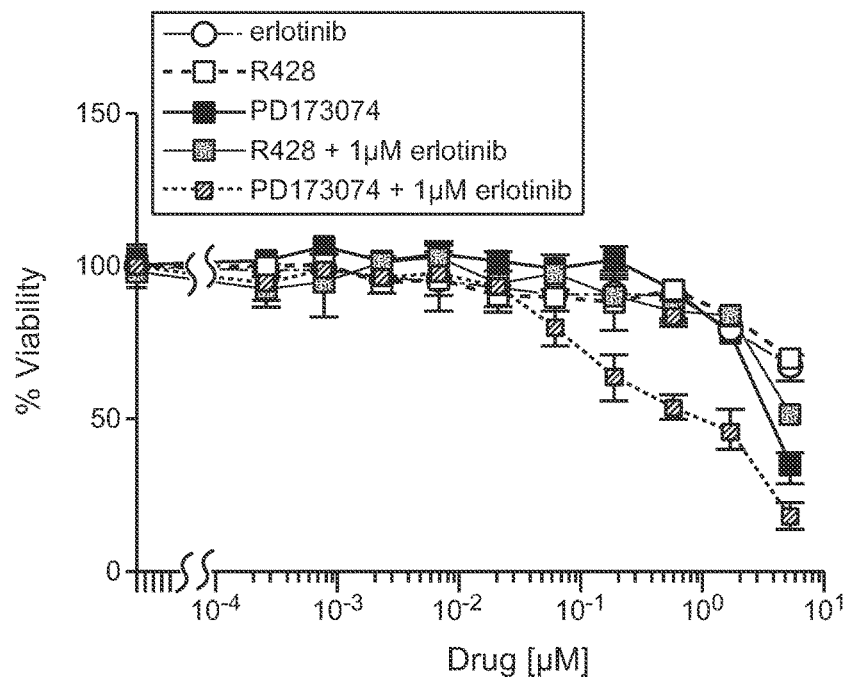
FIG. 7A-B. | FGFR, but not AXL, inhibition partly resensitized another erlotinib-resistant model associated with an EMT, HCC827-ER, to the viability effects of EGFR inhibition. A, Cell viability in HCC827-ER cells was assayed at 72 h in the presence of the indicated concentrations of erlotinib, R428, or PD173074. B, Cell viability in HCC827 and HCC827-ER cells following treatment for 72 h in the presence of recombinant soluble FGFR-Fc to neutralize FGF ligands and controls.
Figure 7B:
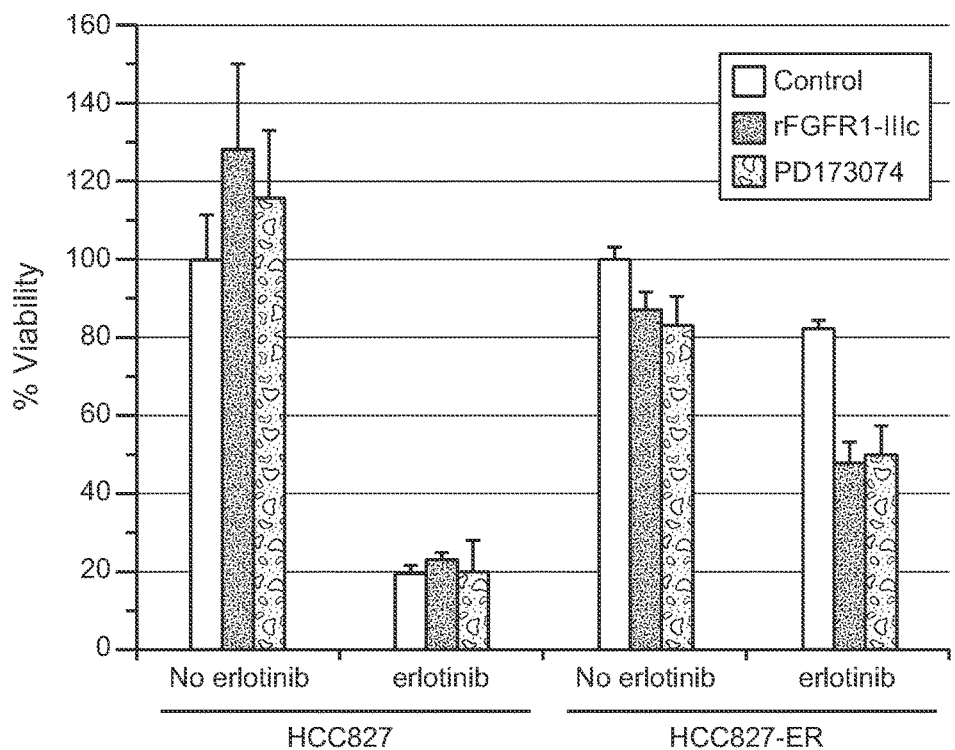

In analysing HCC4006 and HC4006-ER cells, as shown in FIG. 4, FGFR1 and specific FGF ligands were significantly elevated in HCC4006-ER cells based upon microarray profiling and confirmed by qRT-PCR and ELISA. A panel of small molecule inhibitors were screened in HCC4006-ER cells in the presence or absence of erlotinib and revealed that the FGFR inhibitor, PD173074, could reverse resistance to erlotinib. See FIG. 8. Specific inhibition of ligand-dependent FGFR signalling by either the small molecule inhibitor PD173074 or recombinant soluble FGFR-Fc overcame resistance to erlotinib in HCC4006-ER cells as shown in FIG. 5A-C. Further, FGFR inhibition by PD173074 can suppress the development of resistance to erlotinib in HCC4006 cells. See FIG. 6. Consistently, FGFR, but not AXL, inhibition using PD173074 or recombinant soluble FGFR-Fc, as shown in FIG. 7, partly resensitized another erlotinib-resistant model associated with an EMT, HCC827-ER, to the viability effects of EGFR inhibition.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating cancer resistant to an EGFR antagonist comprising administering to an individual in need thereof an effective amount of an antagonist of FGFR signaling and an effective amount of the EGFR antagonist.

2. The method of claim 1, wherein the cancer is non-small cell lung cancer.

3. The method of claim 1, wherein the cancer has undergone epithelial-mesenchymal transition.

4. The method of claim 1, wherein the antagonist of FGFR signaling is an antibody inhibitor, a small molecule inhibitor, a binding polypeptide inhibitor, and/or a polynucleotide antagonist.

5. The method of claim 1, wherein the antagonist of FGFR signaling is an antagonist of FGFR1 signaling.

6. The method of claim 5, wherein the antagonist of FGFR signaling is a binding polypeptide inhibitor, and the binding polypeptide inhibitor comprises a region of the extracellular domain of FGFR linked to a Fc.

7. The method of claim 5, wherein the antagonist of FGFR signaling is a small molecule and the small molecule is N-[2-[[4-(diethylamino)butyl]amino]-6-(3,5-dimethoxyphenyl)pyrido[2,3-d]pyrimidin-7-yl]-N'-(1, 1-dimethylethyl)-urea or pharmaceutically acceptable salt thereof.

8. The method of claim 1, wherein the antagonist of FGFR1 signaling binds to one or more of FGFR1b, FGFR1c, FGF1, FGF2, FGF3, FGF4, FGF5, FGF6, and FGF10.

9. The method of claim 1, wherein the EGFR antagonist is N-(3-ethynylphenyl)-6,7-bis(2-methoxyethoxy)quinazolin-4-amine or a pharmaceutically acceptable salt thereof.

10. The method of claim 1, wherein the EGFR antagonist is N-(3-chloro-4-fluoro-phenyl)-7-methoxy-6-(3-morpholin-4-ylpropoxy)quinazolin-4-amine or a pharmaceutically acceptable salt thereof.

11. The method of claim 1, wherein the antagonist of FGFR signaling is a binding polypeptide inhibitor, and the binding polypeptide inhibitor comprises a region of the extracellular domain of FGFR linked to a Fc, or wherein the EGFR antagonist is N-(3-chloro-4-fluoro-phenyl)-7-methoxy-6-(3-morpholin-4-ylpropoxy)quinazolin-4-amine or a pharmaceutically acceptable salt thereof.

12. The method of claim 1, wherein the antagonist of FGFR signaling is a binding polypeptide inhibitor, and the binding polypeptide inhibitor comprises a region of the extracellular domain of FGFR linked to a Fc, or wherein the antagonist of FGFR signaling is a small molecule and the small molecule is N-[2-[[4-(diethylamino)butyl]amino]-6-(3,5-dimethoxyphenyl)pyrido[2,3-d]pyrimidin-7-yl]-N'-(1, 1-dimethylethyl)-urea or pharmaceutically acceptable salt thereof.

* * * * *